US007402436B2

(12) United States Patent
Yee et al.

(10) Patent No.: US 7,402,436 B2
(45) Date of Patent: Jul. 22, 2008

(54) LENTIVIRAL VECTORS FOR SITE-SPECIFIC GENE INSERTION

(75) Inventors: Jiing-Kuan Yee, Arcadia, CA (US); Gilles Michel, Galveston, TX (US)

(73) Assignee: City of Hope, Duarte, CA (US)

( * ) Notice: Subject to any disclaimer, the term of this patent is extended or adjusted under 35 U.S.C. 154(b) by 281 days.

(21) Appl. No.: 11/121,354

(22) Filed: May 3, 2005

(65) Prior Publication Data

US 2005/0266565 A1     Dec. 1, 2005

Related U.S. Application Data

(60) Provisional application No. 60/567,952, filed on May 3, 2004.

(51) Int. Cl.
| | |
|---|---|
| C12N 15/63 | (2006.01) |
| C12N 15/64 | (2006.01) |
| C12N 15/867 | (2006.01) |
| C07K 14/155 | (2006.01) |
| C07K 14/195 | (2006.01) |
| C07K 19/00 | (2006.01) |
| A61K 48/00 | (2006.01) |

(52) U.S. Cl. .................... 435/455; 435/456; 435/320.1; 530/350

(58) Field of Classification Search ....................... None
See application file for complete search history.

(56) References Cited

U.S. PATENT DOCUMENTS 5,474,896 A * 12/1995 Dujon et al. .................... 435/6

OTHER PUBLICATIONS

Le et al., Nucleic Acids Res., 1999, vol. 27, No. 24, pp. 4703-4709.*
Salmon et al., Molecular Therapy, 2000, vol. 2, No. 4, pp. 404-414.*
Abremski, K., et al. "Studies on the properties of P1 site-specific recombination: evidence for topologically unlinked products following recombination." Cell 32:1301-1311 (1983).
An, D.S., et al. "Marking and gene expression by a lentivirus vector in transplanted human and nonhuman primate CD34+ cells." J Virol 74:1286-1295 (2000).
Bibikova, M., et al. "Enhancing gene targeting with designed zinc finger nucleases." Science 300:764 (2003).
Bibikova, M., et al. "Stimulation of homologous recombination through targeted cleavage by chimeric nucleases." Mol Cell Biol 21:289-297 (2001).
Bibikova, M., et al. "Targeted chromosomal cleavage and mutagenesis in *Drosophila* using zinc-finger nucleases." Genetics 161:1169-1175 (2002).
Buchholz, F., et al. "Alteration of Cre recombinase site specificity by substrate-linked protein evolution." Nat Biotech 19:1047-1052 (2001).
Capecchi, M.R. "Altering the genome by homologous recombination." Science 244:1288-1292 (1989).

Case, S. S., et al. "Stable transduction of quiescent CD34+CD38− human hematopoietic cells by HIV-1-based lentiviral vectors." Proc Natl Acad Sci 96:2988-2993 (1999).
Chandrasegaran, S., et al. "Chimeric restriction enzymes: what is next?" Biol Chem 380:841-848 (1999).
Choulika, A., et al. "Induction of homologous recombination in mammalian chromosomes by using the I-*Sce*I system of *Saccharomyces cerevisiae*." Mol Cell Biol 15:1968-1973 (1995).
Cohen-Tannoudji, M., et al. "I-*Sce*I-induced gene replacement at a natural locus in embryonic stem cells." Mol Cell Biol 18:1444-1448 (1998).
Elliott, B., et al. "Gene conversion tracts from double-strand break repair in mammalian cells." Mol Cell Biol 18:93-101 (1998).
Evans, J. T., et al. "Human cord blood CD34+CD38− cell transduction via lentivirus-based gene transfer vectors." Hum Gene Ther 10:1479-1489 (1999).
Gallay, P., et al. "HIV-1 infection of nondividing cells through the recognition of integrase by the importin/karyopherin pathway." Proc Natl Acad Sci 94:9825-9830 (1999).
Haas, D.L., et al. "Critical factors influencing stable transduction of human CD34+ cells with HIV-1-derived lentiviral vectors." Mol Ther 2:71-80 (2000).
Hacein-Bey-Abina, S., et al. "*LMO2*-associated clonal T cell proliferation in two patients after gene therapy for SCID-X1." Science 302:415-419 (2003).
Heinzinger, N.K., et al. "The Vpr protein of human immunodeficiency virus type 1 influences nuclear localization of viral nucleic acids in nondividing host cells." Proc Natl Acad Sci 91:7311-7315 (1994).
Hoess, R.H., et al. "The role of the *lox*P spacer region in P1 site-specific recombination." Nucleic Acids Res 14:2287-2300 (1986).
Horn, P.A., et al. "Lentivirus-mediated gene transfer into hematopoietic repopulating cells in baboons." Gene Ther 9:1464-1471 (2002a).
Horn, P.A., et al. "Highly efficient gene transfer into baboon marrow repopulating cells using GALV-pseudotype oncoretroviral vectors produced by human packaging cells." Blood 100:3960-3967 (2002b).
Kafri, T., et al. "Sustained expression of genes delivered directly into liver and muscle by lentiviral vectors." Nat Genet 17:314-317 (1997).
Koller, B.H., et al. "Altering genes in animals by gene targeting." Annu Rev Immunol 10:705-730 (1992).
Li, Z., et al. "Murine leukemia induced by retroviral gene marking." Science 296:497 (2002).

(Continued)

*Primary Examiner*—David Guzo
(74) *Attorney, Agent, or Firm*—Michael J. Wise; Perkins Coie LLP

(57) ABSTRACT

Murine leukemia virus (MLV) and lentivirus vectors have been used previously to deliver genes to hematopoietic stem cells (HSCs) in human gene therapy trials. However, these vectors integrate randomly into the host genome, leading to disruption or inactivation of vital host genes. The present invention discloses a novel lentiviral vector system that overcomes this problem by integrating into a host genome in a site-specific manner.

23 Claims, 14 Drawing Sheets

OTHER PUBLICATIONS

Miller, D.G., et al. "Gene transfer by retrovirus vectors occurs only in cells that are actively replicating at the time of infection." Mol Cell Biol 10:4239-4242 (1990).

Miller, M.D., et al. "Human immunodeficiency virus type 1 preintegration complexes: studies of organization and composition." J Virol 71:5382-5390 (1997).

Miyoshi, H., et al. "Transduction of human CD34+ cells that mediate long-term engraftment of NOD/SCID mice by HIV vectors." Science 283:682-686 (1999).

Miyoshi, H., et al. "Stable and efficient gene transfer into the retina using an HIV-based lentiviral vector." Proc Natl Acad Sci 94:10319-10323 (1997).

Mochizuki, H., et al. "High-titer human immunodeficiency virus type 1-based vector systems for gene delivery into nondividing cells." J Virol 72:8873-8883 (1998).

Naldini, L., et al. "Efficient transfer, integration, and sustained long-term expression of the transgene in adult rat brains injected with a lentiviral vector." Proc Natl Acad Sci 93:11382-11388 (1996).

Poeschla, E.M., et al. "Efficient transduction of nondividing human cells by feline immunodeficiency virus lentiviral vectors." Nat Med 4:354-357 (1998).

Popov, S., et al. "Viral protein R regulates docking of the HIV-1 preintegration complex to the nuclear pore complex." J Biol Chem 273:13347-13352 (1998a).

Popov, S., et al. "Viral protein R regulates nuclear import of the HIV-1 pre-integration complex." EMBO J 17:909-917 (1998b).

Porteus, M.H., et al. "Chimeric nucleases stimulate gene targeting in human cells." Science 300:763 (2003).

Richardson, C., et al. "Double-strand break repair by interchromosomal recombination: suppression of chromosomal translocations." Genes Dev 12:3831-3842 (1998).

Rouet, P., et al. "Introduction of double-strand breaks into the genome of mouse cells by expression of a rare-cutting endonuclease." Mol Cell Biol 14:8096-8106 (1994).

Salmon, P., et al. "High-level transgene expression in human hematopoietic progenitors and differentiated blood lineages after transduction with improved lentiviral vectors." Blood 96:3392-3398 (2000).

Sauer, B. "Manipulation of transgenes by site-specific recombination: use of Cre recombinase." Methods Enzymol 225:890-900 (1993).

Sauer, B., et al. "Targeted insertion of exogenous DNA into the eukaryotic genome by the Cre recombinase." New Biol 2:441-449 (1990).

Schroder, A.R., et al. "HIV-1 integration in the human genome favors active genes and local hotspots." Cell 110:521-529 (2002).

Smith, J., et al. "Requirements for double-strand cleavage by chimeric restriction enzymes with zinc finger DNA-recognition domains." Nucleic Acids Res 28:3361-3369 (2000).

Sternberg, N., et al. "Bacteriophage P1 site-specific recombination. I. Recombination between loxP sites." J Mol Biol 150:467-486 (1981b).

Sternberg, N., et al. "Bacteriophage P1 site-specific recombination. II. Recombination between loxP and the bacterial chromosome." J Mol Biol 150:487-507 (1981c).

Sternberg, N. "Bacteriophage P1 site-specific recombination. III. Strand exchange during recombination at lox sites." J Mol Biol 150:603-608 (1981a).

Sutton, R. E., et al. "Human immunodeficiency virus type I vectors efficiently transduce human hematopoietic stem cells." J Virol 72:5781-5788 (1998).

Thomas, K.R., et al. "High frequency targeting of genes to specific sites in the mammalian genome." Cell 44:419-428 (1986).

Thyagarajan, B., et al. "Mammalian genomes contain active recombinase recognition sites." Gene 244:47-54 (2000).

Uchida, N., et al. "HIV, but not murine leukemia virus, vectors mediate high efficiency gene transfer into freshly isolated $G_0/G_1$ human hematopoietic stem cells." Proc Natl Acad Sci USA 95:11939-11944 (1998).

Vanin, E.F., et al. "Development of high-titer retroviral producer cell lines by using Cre-mediated recombination." J Virol 71:7820-7826 (1997).

Woods, N.B., et al. "Lentiviral vector transduction of NOD/SCID repopulating cells results in multiple vector integrations per transduced cell: risk of insertional mutagenesis." Blood 101:1284-1289 (2003).

Wu, X., et al. "Transcription start regions in the human genome are favored targets for MLV integration." Science 300:1749-1751 (2003).

Zheng, H., et al. "Gene targeting in normal and amplified cell lines." Nature 344:170-173 (1990).

\* cited by examiner

A.

B.

A.

B.

A.

B.

A.

B.

A.

B.
accessory protein: Vpr-Cre    Vpr
amounts of virion added: 1x  2X  1x  2X
NP40: − + − + − + − +

0.5 kb →

1　2　3　4　5　6　7　8　9　10

A.

B.

▌: the cleavage site for Vpr-QQR-CN

▢: the modified target site that can no longer be recognized by Vpr-QQR-CN

∗: the mutation in the endogenous gene

SEQUENCE LISTING

<160> NUMBER OF SEQ ID NOS: 2

<210> SEQ ID NO 1
<211> LENGTH: 75
<212> TYPE: DNA
<213> ORGANISM: Artificial
<220> FEATURE:
<223> OTHER INFORMATION: Gene insert containing end of CMV promoter
      sequence, loxP recombination site, and beginning of Neo gene
      sequence
<220> FEATURE:
<221> NAME/KEY: misc_feature
<222> LOCATION: (1)..(3)
<223> OTHER INFORMATION: Final 3 nucleotides of CMV promoter region
<220> FEATURE:
<221> NAME/KEY: misc_feature
<222> LOCATION: (4)..(9)
<223> OTHER INFORMATION: SalI restriction site
<220> FEATURE:
<221> NAME/KEY: misc_feature
<222> LOCATION: (10)..(15)
<223> OTHER INFORMATION: XhoI restriction site
<220> FEATURE:
<221> NAME/KEY: misc_feature
<222> LOCATION: (26)..(59)
<223> OTHER INFORMATION: loxP site
<220> FEATURE:
<221> NAME/KEY: misc_feature
<222> LOCATION: (61)..(70)
<223> OTHER INFORMATION: HindIII/HindIII restriction site
<220> FEATURE:
<221> NAME/KEY: misc_feature
<222> LOCATION: (71)..(75)
<223> OTHER INFORMATION: First 5 nucleotides of Neo gene

<400> SEQUENCE: 1
ccggtcgacc tcgagggatc aattcataac ttcgtatagc atacattata cgaagttatc      60
aagctagctt cacgc                                                      75

<210> SEQ ID NO 2
<211> LENGTH: 9
<212> TYPE: DNA
<213> ORGANISM: Artificial
<220> FEATURE:
<223> OTHER INFORMATION: Recognition sequence for the artificial zinc
      DNA binding domain QQR

<400> SEQUENCE: 2 ggggaagaa                                                              9

LENTIVIRAL VECTORS FOR SITE-SPECIFIC GENE INSERTION

CROSS-REFERENCE TO RELATED APPLICATIONS

This application claims priority to U.S. Provisional Patent Application Ser. No. 60/567,952, filed May 3, 2004, the disclosure of which is incorporated by reference herein in its entirety, including drawings.

FIELD OF INVENTION

The present invention relates to the field of gene delivery, specifically gene delivery using a retroviral vector. More specifically, the present invention relates to the field of gene delivery using a lentiviral vector.

BACKGROUND

Hematopoietic stem cells (HSCs) are pluripotent cells that give rise to all lineages of mature blood cells. HSCs are ideal targets for vector-mediated gene therapy because of their ability for self-renewal and the wide distribution of their progeny. Gene transfer into HSCs has tremendous potential as a means for treating a variety of hematologic and immune disorders.

Retroviral vector systems such as oncoretroviral- and lentiviral-based systems are among the most widely used vector systems for gene therapy. The advantages of retroviral vectors include high efficiency of gene delivery, integration into the host genome, and high levels of gene expression. Vectors derived from murine leukemia virus (MLV), a prototypical oncoretrovirus, have been widely used to deliver genes into HSCs in human gene therapy trials. However, MLV integrates randomly into the host genome, which can lead to gene disruption or unanticipated gene activation through the enhancer or the promoter element in the vector (Li 2002). In a recent gene therapy trial involving the treatment of patients with severe combined immunodeficiency syndrome (SCID), vector integration either near or in the LMO-2 gene resulted in the activation of LMO-2 expression (Hacein-Bey-Abina 2003). This most likely led to leukemia development in two of the nine treated patients. Another drawback to the use of MLV-based vectors is their inability to infect and integrate into non-dividing cells (Miller 1990). This is an issue because HSCs spend the majority of their time in a quiescent state.

Lentiviruses such as human immunodeficiency virus (HIV) differ from oncoretroviruses in that their replicative cycle does not require cell division. This means that the HIV virus can integrate into the genome of non-dividing cells, which partially circumvents the problem of low transduction efficiency in quiescent cells. Upon entry into a host cell, HIV reverse transcriptase generates DNA copies of viral RNA. This DNA is bound to a variety of proteins in a complex called the preintegration complex (PIC). Proteins found in the PIC include nucleocapsid (NCp7), matrix antigen (MA), p6, integrase (IN), Tat and viral protein R (Vpr). Three of these proteins, Ma, In, and Vpr, contribute to the ability of HIV to transduce non-dividing cells, a process that depends on transport of the PIC into the host cell nucleus. Vpr plays a key regulatory role in this nuclear transport by binding to karyopherin α (Popov 1998a), which belongs to a family of cellular proteins involved in active nuclear import (Gallay 1997; Popov 1998b).

HIV vectors have been used to transduce HSCs (Sutton 1998; Uchida 1998; Case 1999; Evans 1999; Miyoshi 1999), hepatocytes (Kafri 1997), neuronal cells (Naldini 1996), and skeletal muscle cells (Kafri 1997). However, transplantation experiments performed in large animals do not support the notion that HIV vectors can transduce hematopoietic repopulating cells more efficiently than MLV vectors (An 2000; Horn 2002a; Horn 2002b). In order to achieve maximum transduction efficiency, a high multiplicity of infection (MOI) is required (Haas 2000; Salmon 2000). However, the use of a high MOI frequently leads to multi-copy vector insertion into host chromosomes (Woods 2003), which increases the risk of cancer due to random vector integration. Vector integration near an oncogene has been linked to an increase in leukemia in SCID patients receiving gene therapy (Hacein-Bey-Abina 2003). In addition, recent studies have shown preferential integration by retrovirus and HIV near or within active genes (Schroder 2002; Wu 2003). These findings underscore the importance of introducing only a limited number of vector copies into the host genome. This can be accomplished by using a low MOI, but this approach reduces transduction efficiency. If HIV vector-mediated gene therapy is going to be successful, it is important to develop approaches for site-specific gene insertion into the host genome.

For targeted integration to avoid insertion mutagenesis, the process of gene replacement by homologous recombination is a very useful but typically inefficient technique (Capecchi 1989). Using this technique in mammalian cells, gene insertion typically only occurs in about 1 out of every $10^6$ cells treated (Capecchi 1989; Koller 1992). For such an event to occur in HSCs, it is almost a prerequisite that a viral vector such as the HIV vector be used, based on its high efficiency of gene transfer into cells. To make gene targeting practical, however, the low frequency of homologous recombination needs to be improved significantly. The use of site-specific recombinases such as Cre has been shown to significantly enhance the efficiency of gene targeting in a mammalian cell environment (Sauer 1993). Cre, a 38-kDa recombinase from bacteriophage P1, utilizes its endonuclease activity to catalyze recombination between two identical loxP sites. The enzyme requires no accessory proteins or cofactors and functions efficiently in vitro and under a wide variety of cellular conditions (Abremski 1983; Sternberg 1981a; Sternberg 1981b; Sternberg 1981c). The recombination site recognized by Cre is a 34-base pair (bp) double-stranded DNA sequence known as loxP. Each loxP site consists of two 13-bp inverted repeats separated by an 8-bp asymmetrical core region. Cre binds to the inverted repeats and cleaves the DNA in the core region to facilitate DNA strand exchange reactions (Abremski 1983; Sternberg 1981a; Sternberg 1981b; Sternberg 1981c). High-level Cre expression in mammalian cells has been shown to mediate site-specific gene insertion at relatively high frequency (Vanin 1997).

SUMMARY OF THE INVENTION

In certain embodiments, the present invention provides a lentiviral-based targeting vector for the insertion of a gene into a host genome in a site-specific manner. This vector includes a lentiviral genomic sequence or some portion thereof, the exogenous polynucleotide to be inserted, and a sequence recognized by a site-specific endonuclease. Cleavage of the vector by the site-specific endonuclease, coupled with cleavage of the host target sequence, facilitates recombination between the vector and the host. In certain of these embodiments, the sequence recognized by an endonuclease may be a loxP site or a pseudo-loxP site. In certain related embodiments, these sequences may be recognition sites for Cre or Cre variants. In certain embodiments, the lentivirus may be HIV. In certain embodiments, the gene to be inserted may be located in the U3 region of the 3' LTR of the HIV genomic sequence. In certain embodiments, the vector may further include one or more reporter genes.

In certain embodiments, the present invention provides another lentiviral-based targeting vector for the insertion of a gene into a host genome in a site-specific manner. This vector includes a lentiviral genomic sequence or some portion thereof, the exogenous polynucleotide to be inserted, and a fusion protein capable of stimulating homologous recombination. In certain of these embodiments, the fusion protein may include a DNA binding domain, preferably a zinc finger binding domain, and an endonuclease domain. In one of these embodiments, the endonuclease domain may be derived from SceI. In certain related embodiments, the fusion protein may include an HIV preintegration complex protein, preferably Vpr, or a portion thereof. In certain embodiments, the lentivirus may be HIV. In certain embodiments, the gene to be inserted may be located in the U3 region of the 3' LTR of the HIV genomic sequence. In certain embodiments, the vector may further include one or more reporter genes.

In certain embodiments, the present invention provides a method for inserting a gene into a host genome in a site-specific manner by transducing a host cell with a lentiviral-based vector that includes the lentiviral genomic sequence or some portion thereof, the exogenous polynucleotide to be inserted, and a sequence recognized by a site-specific endonuclease. In certain of these embodiments, the vector may also include a polypeptide with endonuclease activity. In certain embodiments, this polypeptide may be Cre or a Cre variant. In certain embodiments, the polypeptide may be a fusion protein made up of an HIV preintegration complex protein, preferably Vpr, fused to a site-specific endonuclease, preferably Cre. In certain embodiments, the lentivirus may be HIV.

In certain embodiments, the present invention provides another method for inserting a gene into a host genome in a site-specific manner by transducing a host cell with a lentiviral-based vector that includes the lentiviral genomic sequence or some portion thereof, the exogenous polynucleotide to be inserted, and a fusion protein capable of stimulating homologous recombination. In certain of these embodiments, the lentivirus may be HIV. In certain embodiments, the fusion protein may include a DNA binding domain, preferably a zinc finger binding domain, and an endonuclease domain. In certain of these embodiments, the endonuclease domain may be derived from SceI. In certain related embodiments, the fusion protein may also include an HIV preintegration complex protein, preferably Vpr, or a portion thereof.

In certain embodiments, the present invention provides fusion proteins, consisting of Vpr fused to Cre, Cre variants, SceI, or a chimeric nuclease. The chimeric nuclease is made up of a DNA binding domain attached to an endonuclease domain.

In certain embodiments, the present invention provides polynucleotide sequences encoding fusion proteins consisting of Vpr fused to Cre, Cre variants, SceI, or a chimeric nuclease.

DETAILED DESCRIPTION

Abbreviations

Figure 1:
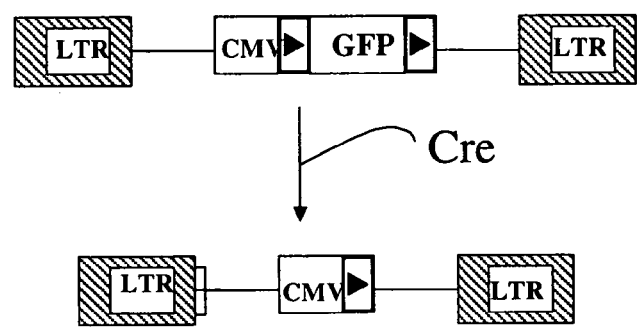
FIG. 1: Creation of a YY2 cell line containing a single loxP site. Human fibrosarcoma HT1080 cells were transduced with an MLV vector containing the green fluorescent protein (GFP) gene flanked by two loxP sites. A. Basic schematic of the MLV vector. GFP expression from this vector was controlled by the immediate early gene promoter of cytomegalovirus (CMV). Large arrowheads (▶) indicate loxP sites. In the presence of Cre, GFP is removed from the vector. B. HT1080 cells were sorted by FACS on the basis of GFP expression both before and after transduction. FACS profiles are shown for non-transduced HT1080 cells (left panel), transduced GFP-positive clone YY1 (center panel), and GFP-negative clone YY2 (right panel), which was created by transfecting YY1 cells with a Cre expression plasmid. The YY2 clone contains a single loxP site.
Figure 1:
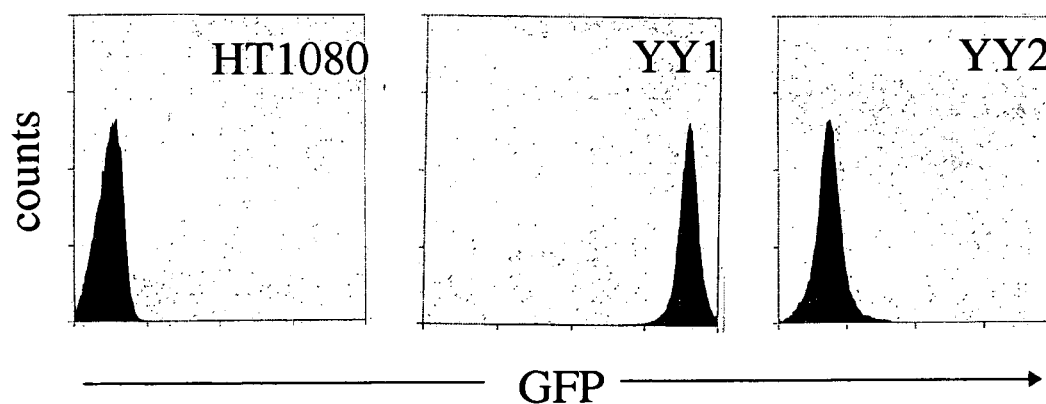

Abbreviations used herein: HSC, hematopoietic stem cell; MLV, murine leukemia virus; HIV, human immunodeficiency virus; SCID, severe combined immunodeficiency syndrome; PIC, preintegration complex; MOI, multiplicity of infection; IE, immediate early; bp, base pair; GFP, green fluorescent protein; LTR, long terminal repeat; kDa, kilodalton; CMV, cytomegalovirus; FACS, fluorescence-activated cell sorting; PCR, polymerase chain reaction; β-gal, β-galactosidase; TK, thymidine kinase; TU, transduction units; AAV, adeno-associated virus; HSV, herpes simplex virus; SV40, simian virus 40 (SV40); CN, chimeric nuclease; FIV, feline immunodeficiency virus; SIV, simian immunodeficiency virus.

Definitions

The term "vector" as used herein refers a vehicle into which a genetic element encoding a polypeptide may be operably inserted so as to bring about the expression of that polypeptide. A vector may be used to transform, transduce or transfect a host cell so as to bring about expression of the genetic element it carries within the host cell. Examples of vectors include plasmids, cosmids, bacmids, bacteriophages such as lambda phage or M13 phage, and animal viruses such as lentivirus, adenovirus, adeno-associated virus (AAV), cytomegalovirus (CMV), herpes simplex virus (HSV), papillomavirus, retrovirus, and simian virus 40 (SV40). A vector utilized as part of an expression system may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. The viral particle may include one or more proteins that help facilitate assembly of the viral particle, transduction of the host cell, and transport of the vector polynucleotide sequence within the host cell, among other functions.

The term "lentiviral-based targeting vector" as used herein refers to a lentiviral vector designed to operably insert an exogenous polynucleotide sequence into a host genome in a site-specific manner. Lentiviral-based targeting vectors may be based on, for example, HIV-1, HIV-2, simian immunodeficiency virus (SIV), or feline immunodeficiency virus (FIV).

In a preferred embodiment, the lentiviral-based targeting vector is an HIV-based targeting vector. This vector may comprise all or a portion of the polynucleotide sequence of HIV.

The term "gene delivery" as used herein refers to the insertion of an exogenous polynucleotide sequence into a host genome such that the polynucleotide sequence is operable.

The term "polynucleotide" as used herein refers to any polyribonucleotide, polydeoxyribonucleotide, or hybrid polyribo-polydeoxyribonucleotide, including naturally occurring polynucleotides, synthetic polynucleotides, or any chemically, enzymatically, or metabolically modified forms of naturally occurring polynucleotides. The term encompasses both single- and double-stranded molecules, including DNA-DNA, DNA-RNA, or RNA-RNA duplexes, as well as molecules that are a mixture of single- and double-stranded regions. Polynucleotides may contain any of the standard pyrimidine or purine bases (i.e., adenine, guanine, cytosine, thymine, uracil), as well as any modified or uncommon bases such as tritylated bases or inosine. In addition, the backbone of a polynucleotide may be modified for stability or for other reasons.

The term "HIV polynucleotide sequence" as used herein refers to all or part of the HIV genomic polynucleotide sequence. The term may refer to the RNA sequence of the HIV virus, or to the DNA sequence resulting from reverse transcription of the HIV genome.

The term "insertion polynucleotide sequence" refers to a polynucleotide sequence that is recognized by one or more recombinase proteins. For example, the term refers to IoxP and pseudo-IoxP sites, which are recognized by the Cre protein.

The term "endonuclease" as used herein refers to an enzyme that is capable of specifically cleaving a DNA strand within a cell, thereby facilitating DNA strand exchange or recombination.

The term "reporter gene" as used herein refers to a gene encoding a product that is readily detectable or measurable when expressed, either directly or indirectly. Examples of reporter genes include, but are not limited to, green fluorescent protein and its variants, β-galactosidase, luciferase, alkaline phosphatase, chloramphenicol acetyltransferase, α-lactamase, and horseradish peroxidase.

The term "polypeptide" as used herein refers to any peptide or protein comprising two or more amino acids joined to each other by peptide bonds or modified peptide bonds, i.e., peptide isosteres. "Polypeptide" refers to both short chains, commonly referred to as peptides, oligopeptides, or oligomers, and to longer chains, generally referred to as proteins. Polypeptides may contain amino acids other than the gene-encoded amino acids. "Polypeptides" include amino acid sequences modified by natural processes, such as posttranslational processing, or by chemical modification using techniques that are well known in the art. Such techniques have been described in basic texts, more detailed monographs, and voluminous research literature. Modifications can occur anywhere in a polypeptide, including the peptide backbone, the amino acid side-chains, and the amino or carboxyl termini. One skilled in the art will recognize that the same type of modification may be present in the same or varying degrees at several sites in a single polypeptide, and that a single polypeptide may contain multiple modifications. Polypeptides may be branched as a result of ubiquitination, and they may be cyclic, with or without branching. Cyclic, branched, and branching cyclic polypeptides may result from posttranslational natural processes, or they may be created by synthetic methods. Polypeptide modifications include acetylation, acylation, ADP-ribosylation, amidation, attachment of an antibody Fc domain (native, recombinant, or humanized), biotinylation, carboxymethylation, covalent attachment of flavin, covalent attachment of a heme moiety, covalent attachment of a lipid or lipid derivative, covalent attachment of a nucleotide or a nucleotide derivative, covalent attachment of phosphotidylinositol, cross-linking, cyclization, dansylation, demethylation, disulfide bond formation, enzyme labeling, farnesylation of cysteine residues, FITC-conjugation, formation of covalent cross links, formation of cystine, formation of pyroglutamate, formylation, gamma-carboxylation, glycosylation, GPI anchor formation, hydroxylation, iodination, methylation, myristoylation, oxidation, pegylation, phosphorylation, prenylation, proteolytic processing, racemization, radiolabeling, selenoylation, succinylation, sulfation, transfer-RNA mediated addition of amino acids to proteins such as arginylation, and ubiquitination. See, for example, Proteins—Structure and Molecular Properties, $2^{nd}$ Ed., T. E. Creighton, W.H. Freeman and Company, New York, 1993; Wold, F., "Posttranslational Protein Modifications: Perspectives and Prospects," pgs. 1-12 in Posttranslational Covalent Modification of Proteins, B. C. Johnson, Ed., Academic Press, New York, 1983; Seifter, S., Englard, S. 1990. Analysis for protein modifications and nonprotein cofactors. Meth Enzymol 182:626-646; Rattan, S. I., Derventzi, A., Clark, B. F. 1992. Protein synthesis: posttranslational modifications and aging. Ann N.Y. Acad Sci 663:48-62.

The term "fusion protein" as used herein refers to a protein consisting of all or part of the amino acid sequences of two or more proteins. Fusion proteins are generally formed by fusing all or a portion of the genes encoding each of the proteins, which results in expression of the fusion protein product.

The term "chimeric nuclease" as used herein refers to a fusion protein consisting of at least one DNA binding domain and at least one endonuclease domain. For instance, the DNA binding domain can be a zinc finger DNA binding domain, and the endonuclease domain can be the SceI protein or a portion thereof.

The term "gene therapy" as used herein refers to a general method for treating a pathologic condition in a subject by inserting an exogenous nucleic acid into an appropriate cell(s) within the subject. The nucleic acid is inserted into the cell in such a way as to maintain its functionality, e.g., maintain the ability to express a particular polypeptide. In certain cases, insertion of the exogenous nucleic acid results in the expression of a therapeutically effective amount of a particular polypeptide.

A "therapeutically effective amount" as used herein refers to an amount of a composition that produces a desired therapeutic effect, such as temporarily or permanently preventing, treating, or improving a condition or alleviating symptoms or indications associated with a condition. Thus, a therapeutically effective amount of a composition is also sufficient to cause a pharmacological effect. A therapeutically effective amount of a composition need not cause permanent improvement or improvement of all symptoms or indications. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), and the type of cell in which a nucleic acid is being inserted. One skilled in the clinical and pharmacological arts will be able to determine a therapeutically effective amount through routine experimentation, namely by monitoring a subject's response to administration of a compound and adjusting the dosage accordingly.

A virus or vector "transduces" a host cell when it transfers nucleic acid into that host cell.

The term "variant" as used herein refers to a polypeptide that differs from a reference polypeptide but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, or deletions in any combination. A substituted or inserted amino acid residue may or may not be one encoded by the genetic code. A variant of a polypeptide may be naturally occurring or it may be a variant that is not known to occur naturally.

Novel Lentiviral Vectors and Uses thereof

Lentiviral vectors are preferable to oncoretroviral vectors for gene delivery in HSCs because they are capable of integrating into non-dividing cells. Lentiviral vectors such as HIV have been used to transduce a variety of cell types, but it has been found that successful transduction requires a high MOI. Unfortunately, the use of a high MOI is likely to result in random gene integration, which can lead to a host of problems such as increased cancer risk. These problems are exacerbated by the tendency of HIV to integrate within active gene sequences. The present invention discloses novel lentiviral vectors that overcome this problem by allowing for site-specific gene integration.

One of the lentiviral vectors disclosed in the present invention contains a IoxP target sequence for the site-specific endonuclease Cre. In order to develop an effective lentiviral vector containing a IoxP site, two primary problems had to be overcome. The first problem was that IoxP sites do not exist in mammalian genomes. However, it has been observed that the human and mouse genomes contain numerous sequences that can support Cre-mediated recombination both in vitro and in vivo just as efficiently as the native IoxP site (Thyagarajan 2000). These sites are referred to as "pseudo-IoxP sites." Although some "pseudo-IoxP" sites diverge significantly from the native IoxP sequence, they nevertheless bind the Cre protein and mediate recombination, making them potential targets for site-specific gene insertion. It has been shown that most nucleotides in the IoxP core region can deviate from the wild-type IoxP sequence, so long as the core nucleotide sequence matches completely between the two recombining IoxP sites (Hoess 1986). The divergence in the core sequences of the mammalian pseudo-IoxP sites provides a means for selective insertion, because an incoming lentiviral vector containing a particular core sequence will only recombine with a pseudo-IoxP site containing the same core sequence.

The second problem that had to be overcome to develop an effective lentiviral vector containing the IoxP site arose specifically when the lentiviral vector was HIV-based. The vector DNA formed after reverse transcription is wrapped in the pre-integration complex (PIC). The PIC of HIV contains not only the double-stranded viral DNA, but also several other proteins including integrase, Vpr, matrix, and the high-mobility group DNA-binding protein HMGI(Y) (Miller 1997). This means that the vector DNA may not be accessible to the Cre protein. The present invention circumvents this problem by generating a Vpr-Cre fusion protein, which is shown to specifically incorporate into HIV vector particles. In addition to solving the accessibility problem, the proximity of the Vpr-Cre protein to the loxP site in the vector DNA may also enhance recombination efficiency.

Another lentiviral vector disclosed in the present invention includes a fusion protein for stimulating recombination. A major impediment to efficient homologous recombination is the status of the chromosomal target. An increase in the number of target sequences has little or no effect on targeting efficiency (Thomas 1986; Zheng 1990). In contrast, making an intentional double-strand break in the target DNA increases the yield of specific homologous recombination events up to 1,000 fold or more (Rouet 1994; Choulika 1995; Cohen-Tannoudji 1998; Elliott 1998; Richardson 1998). Previous studies have shown that insertion of an artificial gene target containing the recognition site for the I-SceI endonuclease into the genome of human 293 cells results in gene targeting rates of 3-5% when the treated DNA was previously cleaved by SceI (Porteus 2003). The drawback to this type of system is that it depends on prior introduction of a SceI recognition site into the target gene, and thus cannot be used for endogenous genes. This limitation can be overcome by the use of chimeric nucleases, which have the potential to create sequence-specific double-stranded breaks (Chandrasegaran 1999). Chimeric nucleases consisting of zinc finger DNA binding domains fused to endonuclease domains that recognize specific endogenous DNA sequences can site-specifically cleave naked DNA in vitro (Chandrasegaran 1999), extrachromosomal DNA in *Xenopus oocytes* (Bibikova 2001), and chromosomal DNA in *Drosophila* (Bibikova 2002). In addition, an artificial zinc finger binding domain fused to an endonuclease has been shown to significantly stimulate gene targeting in human cells (Buchholz 2001). The ability to control the recognition specificity of zinc fingers opens the prospect of directing cleavage to arbitrarily chosen chromosomal sites without prior manipulation of the target. The present invention utilizes chimeric nucleases fused to viral proteins such as Vpr to facilitate site-specific polynucleotide insertion. The presence of Vpr in these fusion proteins allows them to be incorporated into the lentiviral virion, where they facilitate site-specific cleavage of genomic DNA and enhance the efficiency of homologous recombination.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1

Creation of a YY2 Cell Line Containing a Single loxP Site

To test site-specific gene insertion by the HIV-based targeting vector, a cell line was established containing a single loxP site to serve as the target for HIV vector-mediated gene insertion. Human fibrosarcoma HT1080 cells were transduced with an MLV vector containing the green fluorescent protein (GFP) gene flanked by two loxP sites. GFP expression from this vector was controlled by the immediate early (IE) gene promoter of CMV. A basic schematic of this vector is shown in FIG. 1A. Transduced cells were sorted by FACS on the basis of GFP expression, and a single GFP-positive clone (YY1) was selected for study. YY1 expressed high levels of GFP in comparison to the parental HT1080 cells (FIG. 1B). Southern blot analysis indicated that YY1 cells contained only a single copy of the proviral genome (data not shown).

Figure 2:
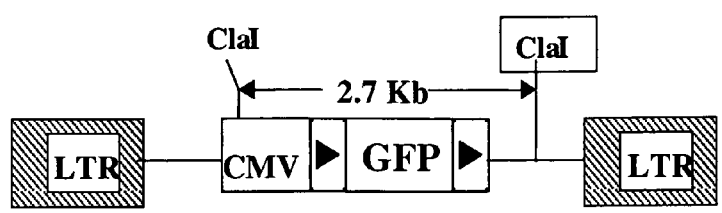
FIG. 2: Southern blot analysis of transduced YY cells. Chromosomal DNA from HT1080, GFP-positive YY1, GFP-negative YY2, and GFP-negative YY3 cells was digested with ClaI and analyzed by Southern blot. A. Basic schematic illustrating expected fragments generated by ClaI digestion of YY1 DNA (upper schematic) and YY2 (lower schematic). Large arrowheads (▶) indicate loxP sites. B. Southern blotting was performed using either a CMV promoter sequence (left panel) or a GFP gene sequence (right panel) as the probe. The lanes are designated as follows: 1) non-transduced HT1080 cells; 2) YY1 cells; 3) YY2 cells; 4) YY3 cells. YY1 cells exhibited a 2.7-kb fragment that hybridized with both the CMV and GFP probes. YY2 and YY3 cells exhibited a 1.9-kb fragment that hybridized with the CMV probe but not the GFP probe, indicating removal of the GFP gene.
Figure 2:
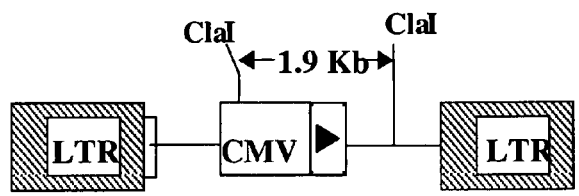
Figure 2:
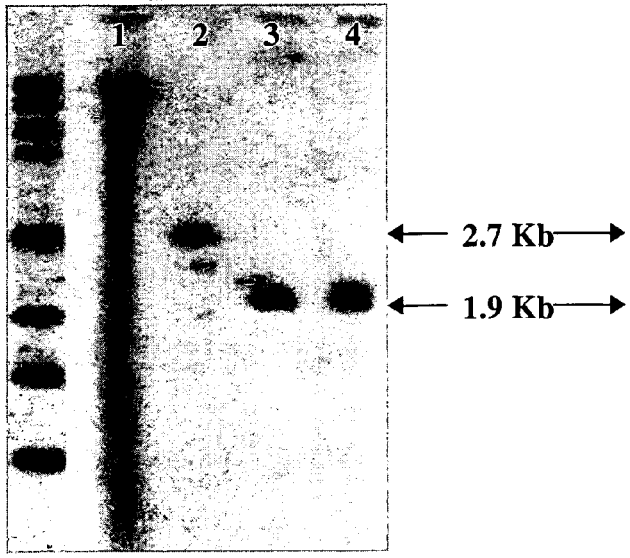
Figure 2:
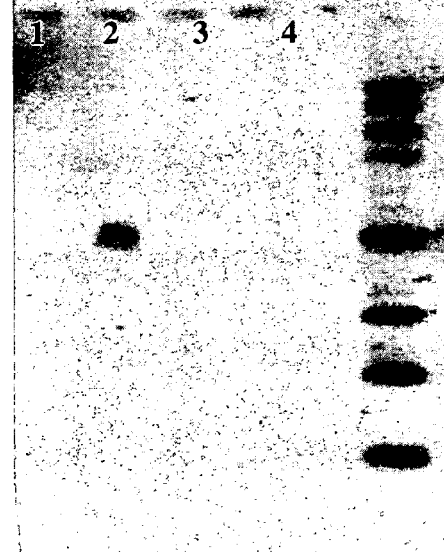

To generate the target loxP site for gene insertion, YY1 cells were transfected with pBS185, a Cre expression plasmid (Sauer 1993) kindly provided by Dr. Brian Sauer (E.I. Du Pont, Wilmington, Del.). Cells were again sorted by FACS on the basis of GFP expression, and two independent GFP-negative clones were selected (YY2 and YY3). The FACS profile for one of these clones, YY2, is shown in FIG. 1B. Chromosomal DNA from YY1, YY2, and YY3 was digested with ClaI and subjected to Southern blot analysis using either a CMV promoter sequence or the GFP gene sequence as a probe. YY1 cells exhibited the expected 2.7-kb fragment containing both the CMV and GFP sequences (FIG. 2B, lane 2). YY2 and YY3 exhibited a 1.9-kb fragment that hybridized with the CMV probe but not with the GFP probe (FIG. 2B, lanes 3 & 4), indicating removal of the GFP gene by Cre treatment. The YY2 cells, which contain the CMV IE promoter followed by a single loxP site, were chosen as a target for site-specific gene insertion.

To determine whether the loxP site in YY2 cells is suitable to serve as a target for site-specific gene insertion, the cells were transfected with a plox-geo vector in the presence or absence of pBS185, a Cre expression plasmid. The plox-geo vector contains the geo gene flanked by two loxP sites. The geo gene encodes a fusion protein consisting of neomycin phosphotransferase (neo) and β-galactosidase (β-gal). Cells expressing geo are G418 resistant and express β-gal. Since the plox-geo vector contains neither a promoter nor a polyadenylation signal, random insertion into host chromosomes is unlikely to confer G418 resistance. In the presence of Cre, however, the geo gene should insert into the loxP site in YY2 cells and become expressed, conferring G418 resistance on the host cell.

Control YY2 cells transfected with a pTK-neo vector containing the neo gene under the control of the herpes thymidine kinase (TK) promoter generated 20 G418-resistant colonies. YY2 cells transfected with the plox-geo vector alone generated no G418 resistant colonies, but YY2 cells co-transfected with both the plox-geo vector and the pBS185 Cre expression plasmid generated 27 G418-resistant colonies (Table 1, below). This suggests that in the presence of Cre, the geo gene is being inserting into the loxP site of YY2 cells.

TABLE 1

| Plasmid | Number of G418-resistant colonies |
| --- | --- |
| pTK-neo | 20 |
| plox-geo | 0 |
| plox-geo + pBS185 | 27 |

Figure 3:
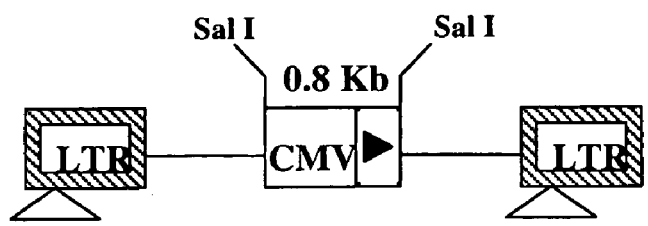
FIG. 3: Southern blot analysis of plox-geo/pBS185 co-transfected YY2 cells. YY2 cells were transfected with a plox-geo vector in the presence or absence of the Cre expression plasmid pBS185. The plox-geo vector contains the geo gene, which confers G418 resistance, flanked by two loxP sites. YY2 cells transfected with plox-geo and pBS185 exhibited G418 resistance, suggesting that the geo gene was being inserted into the YY2 loxP site. To confirm that this insertion was site-specific, chromosomal DNA from HT1080, YY2, and plox-geo/pBS185 co-transfected YY2 cells was digested with SalI and EcoRI and analyzed by Southern blot. A. Basic schematic of the loxP site in YY2 cells (upper schematic) and the same region following insertion of the geo gene (lower schematic). The schematics illustrate the expected fragments generated by SalI and EcoRI digestion. Large arrowheads (▶) indicate loxP sites. B. Southern blotting was performed using a CMV promoter sequence as the probe. The lanes are designated as follows: 1) HT1080 cells; 2) YY2 cells; 3-6) four independent G418-resistant YY2 clones. YY2 cells exhibited the expected 0.8-kb fragment, while each of the four G418-resistant clones exhibited the expected 3.2-kb fragment.
Figure 3:
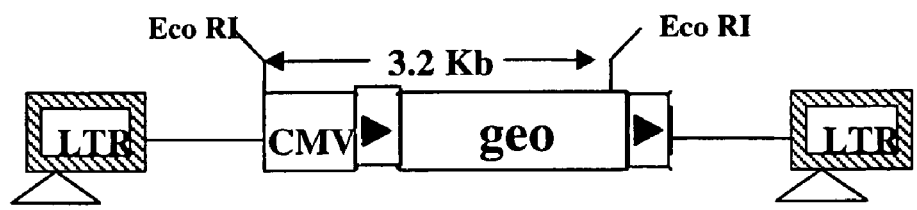
Figure 3:
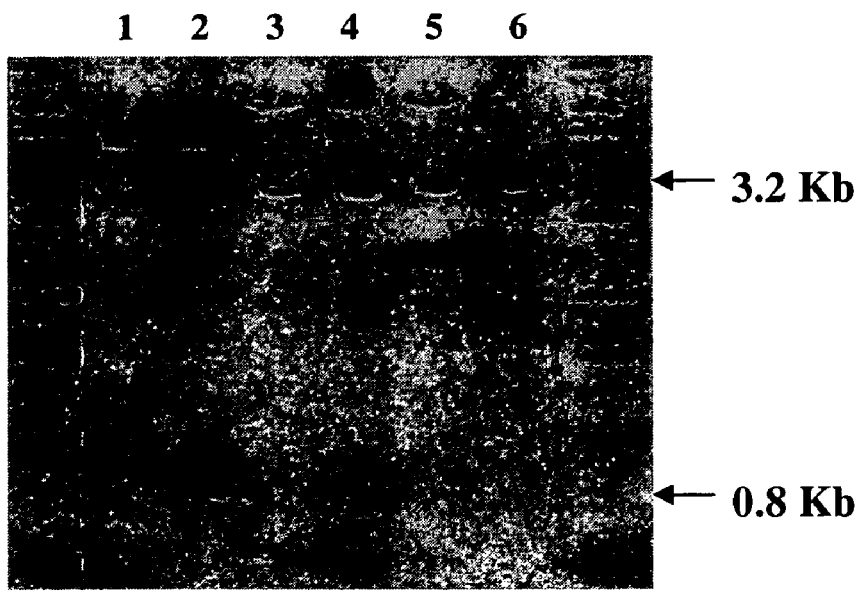

To confirm that insertion of the geo gene is site-specific, chromosomal DNA from four of the 27 G418-resistant clones was digested with EcoRI and SalI and subjected to Southern blot analysis using the CMV IE promoter fragment as a probe. All four G418-resistant clones exhibited an expected 3.2-kb fragment when digested with EcoRI (FIG. 3, lanes 3-6), confirming site-specific insertion of the geo gene into the loxP site. YY2 exhibited an expected 0.8-kb fragment when digested with SalI (FIG. 3, lane 2). These results confirm the suitability of the single loxP site in YY2 cells as a target for site-specific gene insertion.

Example 2

Incorporation of Cre Protein into HIV Viral Particles

HIV vector DNA is wrapped in the PIC following reverse transcription, making it difficult for Cre to access the DNA for site-specific insertion. To overcome this problem, Cre was incorporated into HIV particles as a fusion protein with Vpr. Vpr is an HIV accessory protein that is efficiently incorporated into HIV particles. Vpr is also a component of the PIC, serving to actively mediate HIV-1 viral DNA nuclear transport (Heinzinger 1994). This means that Vpr is likely to be in close contact with viral DNA during viral infection and replication. It was hypothesized that fusion of Cre to Vpr might enable Cre to be incorporated into HIV vector particles. If the HIV vector also includes a gene of interest containing a loxP site, the close proximity of the Vpr-Cre fusion protein and this loxP site may facilitate the interaction between these two components. This in turn may allow for more efficient insertion of the gene of interest into loxP sites within the host genome.

Figure 4:
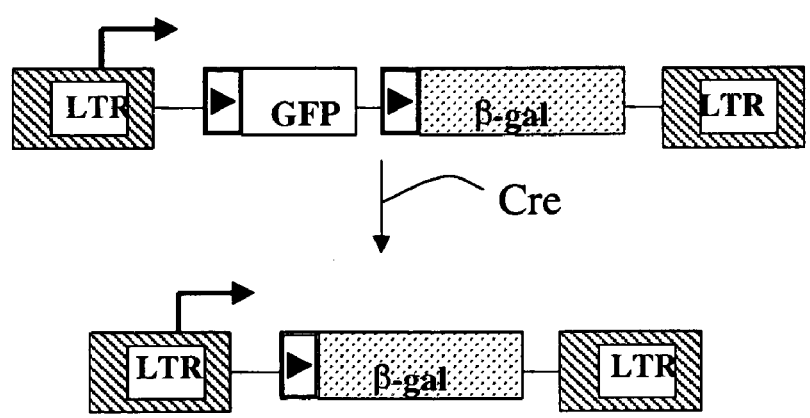
FIG. 4: Analysis of Vpr-Cre fusion protein activity. The stable cell line HT1080/Gβ, which had previously been transduced with a retroviral vector containing both GFP and β-gal genes, was co-transfected with either a Cre or a Vpr-Cre expression plasmid. A. Basic schematic of the retroviral vector transduced into HT1080/Gβ cells. Large arrowheads (▶) indicate loxP sites. In the presence of Cre, GFP is removed from the vector, which activates β-gal expression. B. β-gal activity of HT1080/Gβ transfectants was determined 48 hours later after transfection. Mock-transfected HT1080/Gβ cells (−) displayed background levels of β-gal activity, while cells transfected with the Cre or Vpr-Cre expression plasmids exhibited efficient β-gal activity. β-gal activity was lower in cells transfected with Vpr-Cre than in cell transfected with Cre, suggesting that Vpr fusion may compromise Cre function to some extent.
Figure 4:
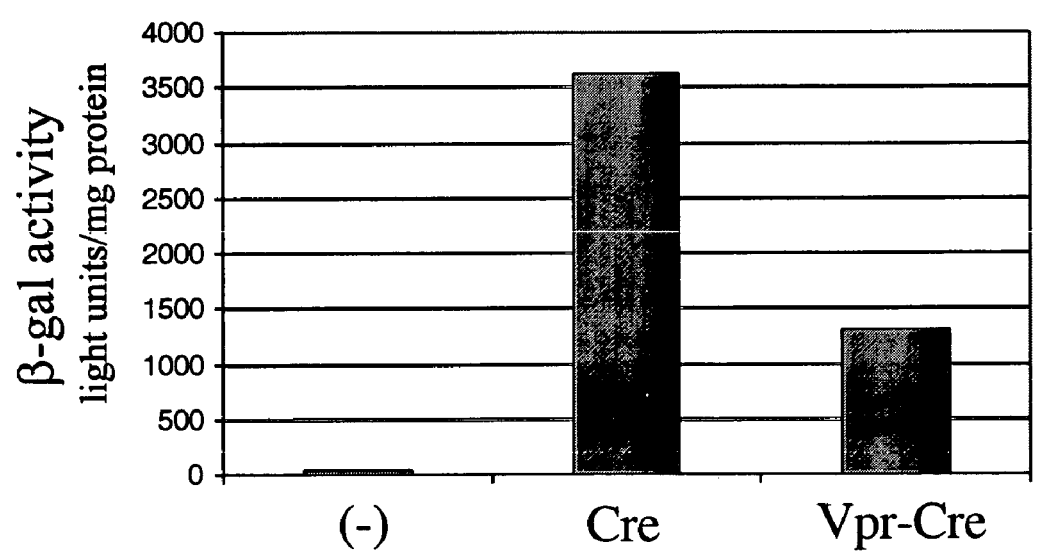

A gene encoding the Vpr-Cre fusion protein was constructed. The protein encoded by this gene consisted of the 96-amino acid Vpr protein attached to the amino terminus of the Cre protein. To assay for Cre function in this fusion protein, a stable cell line (HT1080/Gβ) was established by transducing human fibroblastoma HT1080 cells with a retroviral vector containing both the GFP and β-gal genes. HT1080/Gβ cells express GFP, but β-gal expression is blocked by the presence of the upstream GFP reading frame. Since the GFP gene is flanked by two loxP sites, Cre-mediated recombination to remove the GFP gene will activate β-gal expression. In this manner, the HT1080/Gβ cell line allows for quantitative analysis of Cre activity. HT1080/Gβ cells were transiently transfected with either a Cre or a Vpr-Cre expression plasmid, and the β-gal activity of the transfectants was determined 48 hours later. Mock-transfected HT1080/Gβ cells displayed background levels of β-gal activity, while cells transfected with the Cre or Vpr-Cre expression plasmids exhibited efficient β-gal activity (FIG. 4B). Cells transfected with the Vpr-Cre plasmid exhibited less β-gal activity than cells transfected with Cre, suggesting that the presence of Vpr may compromise Cre function to some extent.

Figure 5:
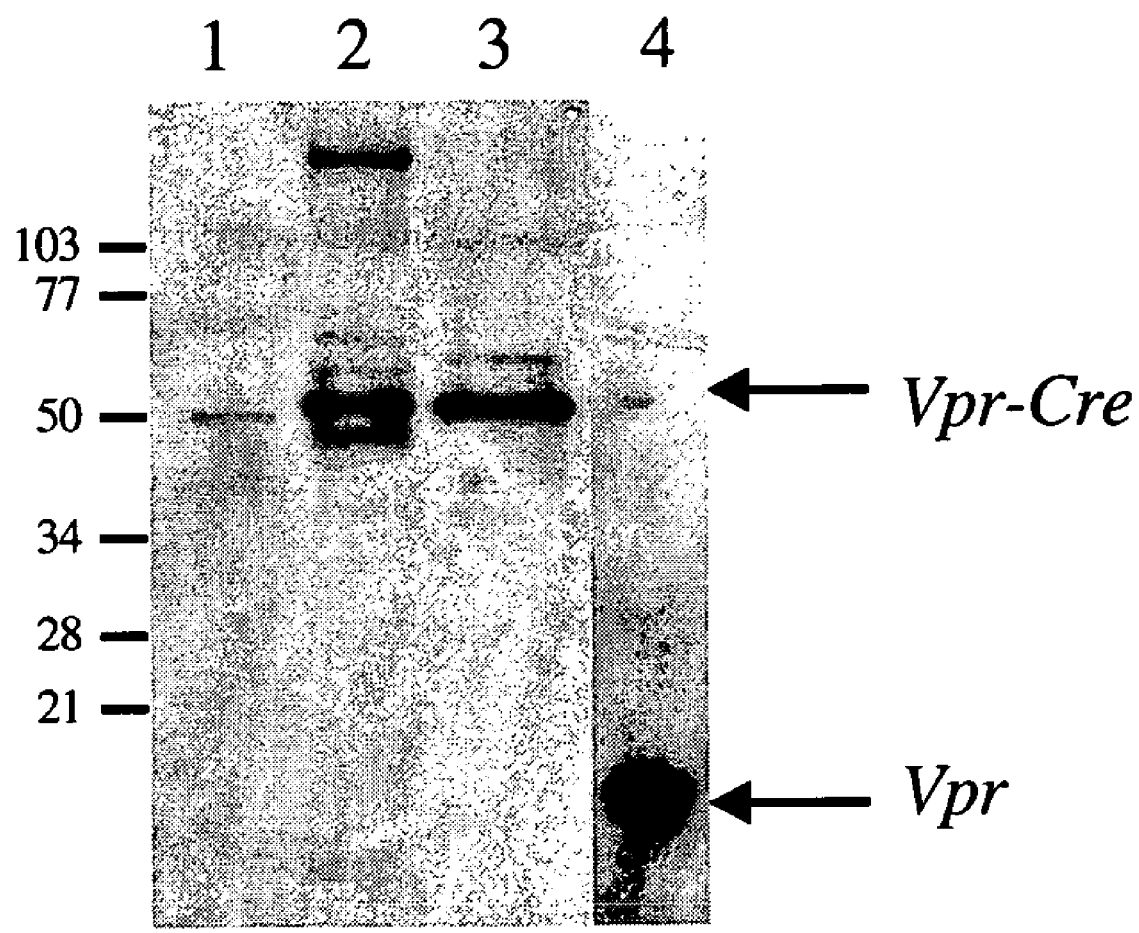
FIG. 5: Incorporation of Vpr-Cre into HIV vector particles. HIV vector particles were generated by transfecting 293T cells with an HIV packaging plasmid in the presence or absence of a Vpr-Cre expression plasmid. The HIV packaging plasmid was either pCMV-HIV-1 or pCMV-HIVΔvpr. pCMV-HIVΔvpr is an HIV packaging plasmid in which the gene encoding Vpr has been inactivated. Viral particles were harvested, purified, and analyzed by Western blot. Lanes are designated as follows: 1) vector particle generated from pCMV-HIVΔvpr in the absence of Vpr-Cre; 2) vector particle generated from pCMV-HIVΔvpr in the presence of Vpr-Cre; 3) extract of 293T cells transfected with pCMV-HIVΔvpr in the presence of Vpr-Cre; and 4) vector particle generated from pCMV-HIV-1.

To determine whether Vpr-Cre can be incorporated into HIV particles, HIV vector particles were generated by transfecting 293T cells with an HIV packaging plasmid in the presence or absence of the Vpr-Cre expression plasmid. To minimize competition with wild-type Vpr for particle incorporation, the wild-type vpr gene in the packaging plasmid, pCMV-HIV-1, was inactivated by a frameshift mutation to generate pCMV-HIVΔvpr. Vector particles were harvested, purified by centrifugation through a sucrose cushion, and analyzed by Western blotting using a Vpr-specific antibody. A 50-kilodalton (kDa) protein, consistent with the expected size of the Vpr-Cre fusion protein, was observed in the vector particle that was generated in the presence of the Vpr-Cre expression plasmid (FIG. 5, lane 2). The cell extract from the 293T cells producing these vector particles also exhibited a 50 kDa reactive band (FIG. 5, lane 3). Vector particles generated in the absence of the Vpr-Cre expression plasmid did not exhibit such a band (FIG. 5, lane 1). These results suggest that Vpr-Cre can be packaged into the HIV particle in the absence of wild-type Vpr.

Figure 6:
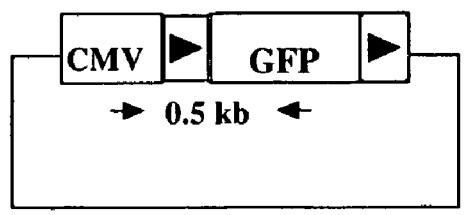
FIG. 6: In vitro Vpr-Cre-mediated recombination in the presence and absence of NP40. To exclude the possibility that Vpr-Cre simply sticks to the outside of the virus particle, purified viral particles were subjected to an in vitro Cre-mediated recombination assay. HIV viral particles containing either Vpr or Vpr-Cre were treated with 0.5% NP40, then incubated with a plasmid containing the GFP gene flanked by two loxP sites at 37° C. for 30 minutes in the presence of with 10 mM $MgCl_2$. A. Basic schematic of the plasmid containing the GFP gene. Large arrowheads (▸) indicate loxP sites. Small arrowheads indicate the PCR amplified region. B. Recombination was monitored by PCR amplification of a 0.5-kb region of the GFP gene. Lanes are designated as followed: 1) DNA size standards; 2) viral particle containing Vpr-Cre, 1× virion concentration; 3) viral particle containing Vpr-Cre, NP40 treated, 1× virion concentration; 4) viral particle containing Vpr-Cre, 2× virion concentration; 5) viral particle containing Vpr-Cre, NP40 treated, 2× virion concentration; 6) viral particle containing wild-type Vpr, 1× virion concentration; 7) viral particle containing wild-type Vpr, NP40 treated, 1× virion concentration; 8) viral particle containing wild-type Vpr, 2× virion concentration; 9) viral particle containing wild-type Vpr, NP40 treated, 2× virion concentration; 10) DNA size standards.
Figure 6:
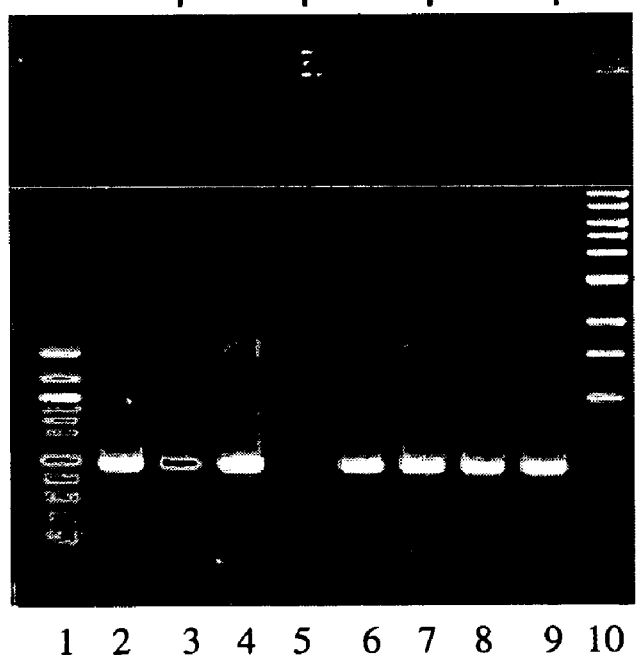

To exclude the possibility that Vpr-Cre simply sticks to the outside of the virus particle, purified vector particles were subjected to an in vitro Cre-mediated recombination assay. HIV vector particles containing either Vpr or Vpr-Cre were treated with 0.5% NP40 to allow the release of the incorporated protein. Following NP40 treatment, the particles were incubated with a plasmid containing the GFP gene flanked by two loxP sites, in the presence of 10 mM $MgCl_2$, for 30 minutes at 37° C. Recombination was monitored by PCR amplification of a 0.5-kb region of the GFP gene. In the absence of Cre, this PCR reaction will result in a 0.5-kb fragment. In the presence of Cre, however, this fragment will be absent due to GFP gene deletion. Viral particles containing wild-type Vpr generated no recombination, as indicated by the presence of the expected 0.5-kb fragment in both the presence and absence of NP40 treatment (FIG. 6, lanes 6-9). The 0.5-kb fragment was also observed in viral particles containing Vpr-Cre, but only in the absence of NP40 treatment (FIG. 6, lanes 2 and 4). Following NP40 treatment, the 0.5-kb fragment decreased in the Vpr-Cre 1× viral sample (FIG. 6, lane 3) and disappeared entirely in the Vpr-Cre 2× viral sample (FIG. 6, lane 5). These results suggest that Vpr-Cre was incorporated into the vector particle and released upon NP40 treatment to generate the in vitro recombination reaction.

To determine whether Vpr-Cre incorporated into HIV viral particles can mediate recombination in vivo, a retroviral vector containing the GFP gene and either Vpr or Vpr-Cre was used to transduce HT1080/Gβ cells. Transduction with the Vpr-containing vector generated no β-gal-positive cells, while transduction with the Vpr-Cre-containing vector produced cells with substantial β-gal activity (Table 2, below). This suggests that the incorporated Vpr-Cre protein remains enzymatically active in vivo. The titer of the vector containing Vpr-Cre as determined by β-gal activity was $3.7 \times 10^5$ transduction units (TU)/ml (Table 2, below). When the same vector was titered in HT1080 cells by GFP expression, it was determined to be $3.0 \times 10^7$ TU/ml. The difference between the two titers can be explained by the fact that not every infectious vector particle incorporated sufficient Vpr-Cre to mediate efficient recombination in HT1080/Gβ cells. The appearance of β-gal-positive cells required viral infection, because the Vpr-Cre-containing vector did not induce β-gal in the absence of VSV-G envelope (Table 2, below).

TABLE 2

| Vector | Vector titer (TU/ml) as determined by GFP expression in HT1080 cells | Vector titer (TU/ml) as determined by β-gal activity in HT1080/Gβ cells |
| --- | --- | --- |
| GFP/Vpr | $5.5 \times 10^6$ | — |
| GFP | $1.4 \times 10^7$ | — |
| GFP/Vpr-Cre | $3.0 \times 10^7$ | $3.7 \times 10^5$ |
| GFP/Vpr-Cre in the absence of VSV-G | — | — |

The approach utilized herein to incorporate Cre into HIV viral particles should be generally applicable to all Cre variants. Molecular evolution has been used previously to generate Cre variants that recognize a new DNA target sequence present in human chromosomes (Buchholz 2001). These Cre variants and any other variant derived to recognize specific human DNA sequences can potentially be incorporated into HIV virions using the Vpr fusion approach, thereby generating a panel of fusion proteins that direct site-specific gene targeting into human chromosomes.

Example 3

Site-Specific Gene Targeting by an HIV Vector

Figure 7:
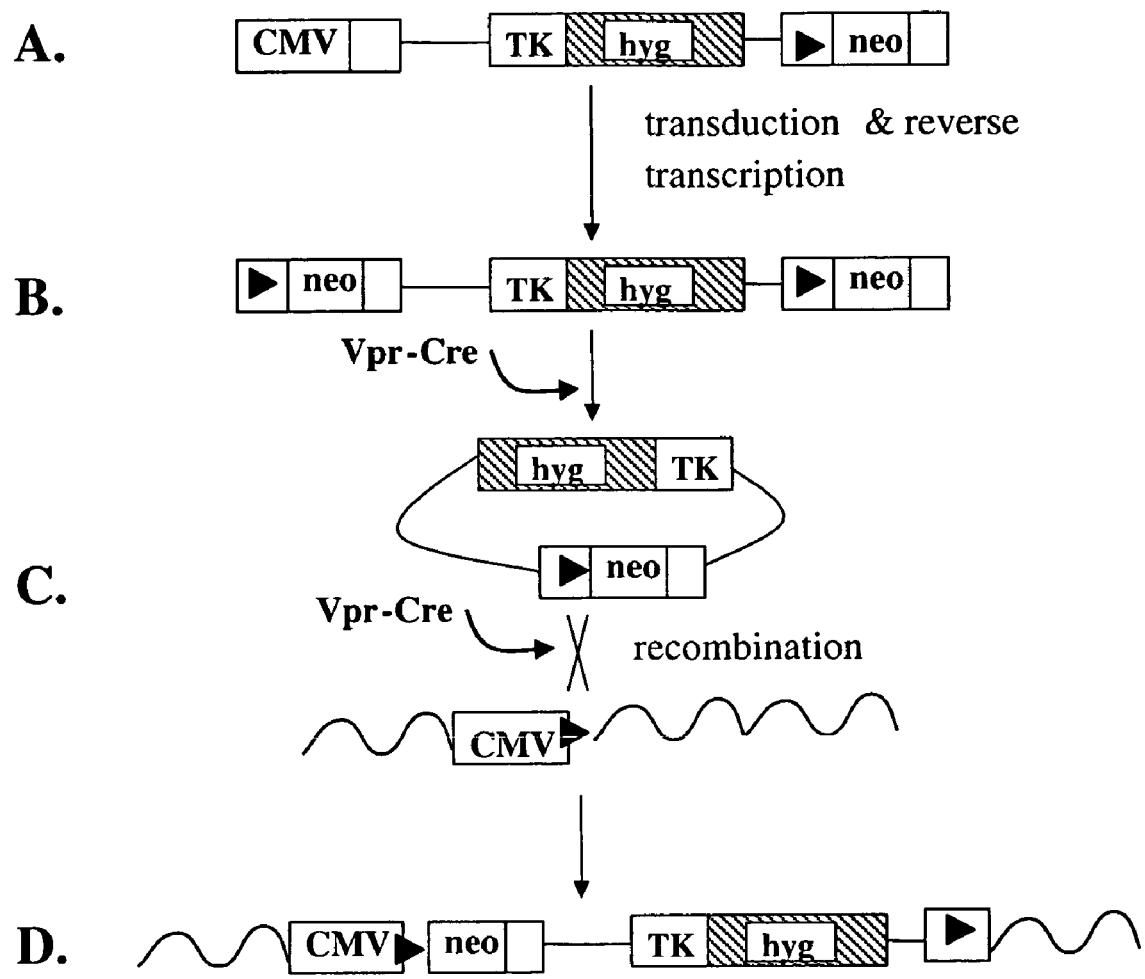
FIG. 7: Mechanism of site-specific gene insertion. A. An exogenous polynucleotide sequence containing the neo gene preceded by a single loxP site (▸) was inserted into the 3' LTR of pHIV7 to produce the targeting vector. Since the neo gene contains no promoter, a TK-hyg polynucleotide sequence containing the hygromycin-resistant gene controlled by the herpes TK promoter was also inserted for vector titering. B. Following transduction, the neo/loxP polynucleotide sequence appears in both the 5' LTR and 3' LTR, because the U3 region in the 3' LTR serves as the template for the generation of U3 in both LTRs during reverse transcription. C. In transduced cells, recombination takes place between the two loxP sites in the HIV vector in the presence of Vpr-Cre to generate a neo-containing circular DNA in the pre-integration complex (PIC). The neo-containing circular DNA is then transported into the nucleus and inserted into the target loxP site in the YY2 genome in the presence of Vpr-Cre. D. The end result is site-specific insertion of that portion of the HIV vector containing the neo and hyg genes into YY2 genomic DNA.

To test for site-specific gene insertion, an exogenous polynucleotide sequence containing the neo gene preceded by a single IoxP site was inserted into the 3' LTR of pHIV7 (FIG. 7A). Since the neo gene contains no promoter, only site-specific insertion of the gene into the IoxP site in YY2 cells would place the gene under the control of the CMV IE promoter and confer G418-resistance to the cells. Only a single IoxP-neo polynucleotide sequence was inserted into the U3 region of the 3' LTR because Vpr-Cre expression in vector-producing 293T cells would remove any neo gene flanked by two IoxP sites. Upon transduction, the same neo polynucleotide sequence will appear in both LTRs, because the U3 region in the 3' LTR serves as the template for the generation of U3 in both LTRs during reverse transcription (FIG. 7B). It was hypothesized that in the transduced cells, recombination would take place between the two IoxP sites in the HIV vector in the presence of Vpr-Cre to generate a neo-containing circular DNA in the PIC (FIG. 7C). The circular DNA in the PIC would then be transported into the nucleus and inserted into the target IoxP site in the YY2 genome (FIG. 7C and 7D). Since the neo gene contained no promoter, a TK-hyg polynucleotide sequence containing the hygromycin-resistant gene controlled by the herpes TK promoter was inserted for vector titering (FIG. 7A).

Figure 8:
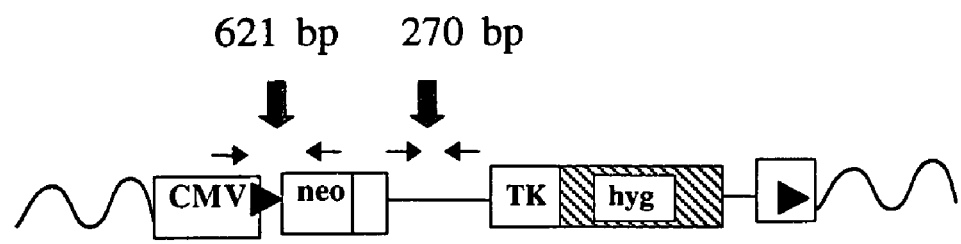
FIG. 8: PCR detection of site-specific gene insertion. Colonies of YY2 cells containing a Cre-mediated site-specific gene insertion were selected based on G418 resistance. G418-resistant colonies were pooled, and the genomic DNA was extracted for PCR analysis to confirm site-specific gene insertion. A. Basic schematic of the gene insertion in YY2 cells. Large arrowheads (▸) indicate loxP sites. The first set of small arrowheads ("621 bp") indicates the region amplified by primer set 1. This primer pair was used to confirm insertion. The second set of small arrowheads ("270 bp") indicates the region amplified by primer set 2. This primer pair was used as a control. B. PCR analysis of site-specific gene insertion. Lanes are designated as follows: 1) size standards; 2) DNA from 125 G418-resistant colonies amplified by primer set 1; 3) DNA from 250 G418-resistant colonies amplified by primer set 1; 4) DNA from 2,500 G418-resistant colonies amplified by primer set 1; 5) DNA from non-transduced YY2 cells amplified by primer set 1; 6) DNA size standards 7) DNA from 125 G418-resistant colonies amplified by primer set 2; 8) DNA from 250 G418-resistant colonies amplified by primer set 2; 9) DNA from 2,500 G418-resistant colonies amplified by primer set 2.
Figure 8:
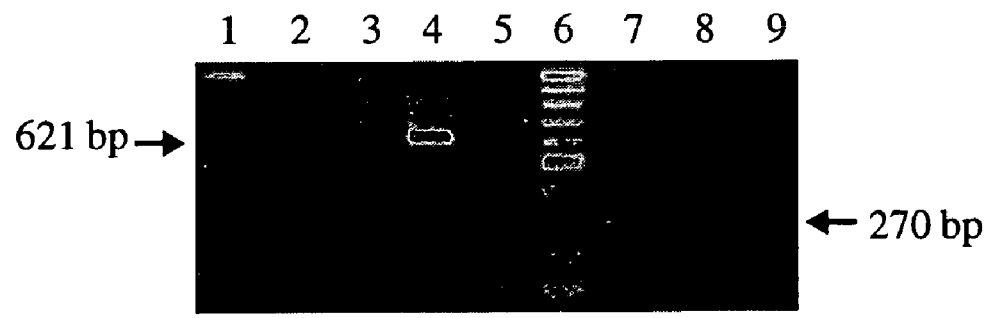

The targeting vector was prepared from 293T cells with either wild-type Vpr or Vpr-Cre. Incorporation of the Vpr-Cre proteins was confirmed by transducing HT1080/Gβ cells and staining the cells for β-gal expression (data not shown). YY2 cells containing a single copy of the IoxP site preceded by the CMV IE promoter were transduced with the targeting vector and selected in G418 containing media. Various G418-resistant colonies were pooled, and the genomic DNA was extracted for PCR amplification to detect site-specific gene targeting. The first pair of PCR primers included a CMV IE promoter-specific primer and a neo gene-specific primer. Cre-IoxP-mediated gene targeting was expected to generate a 621-bp PCR fragment using these two primers. No PCR product was detected using DNA isolated from untransduced YY2 cells (FIG. 8, lane 5). In contrast, the expected 621-bp PCR product was observed using the genomic DNA of approximately 2,500 pooled G418-resistant colonies derived from YY2 cells transduced with the Vpr-Cre-containing vector (FIG. 8, lane 4). A weak band at the same position was observed using the genomic DNA sample from 250 pooled colonies (FIG. 8, lane 3) but not using the genomic DNA from 125 pooled colonies (FIG. 8, lane 2). PCR reactions with two other primer pairs confirmed these results (data not shown). A control PCR reaction was performed using a primer pair that amplified a 270-bp fragment, in order to confirm equal DNA loading in each PCR reaction (FIG. 8, lanes 7-9).

Figure 9:
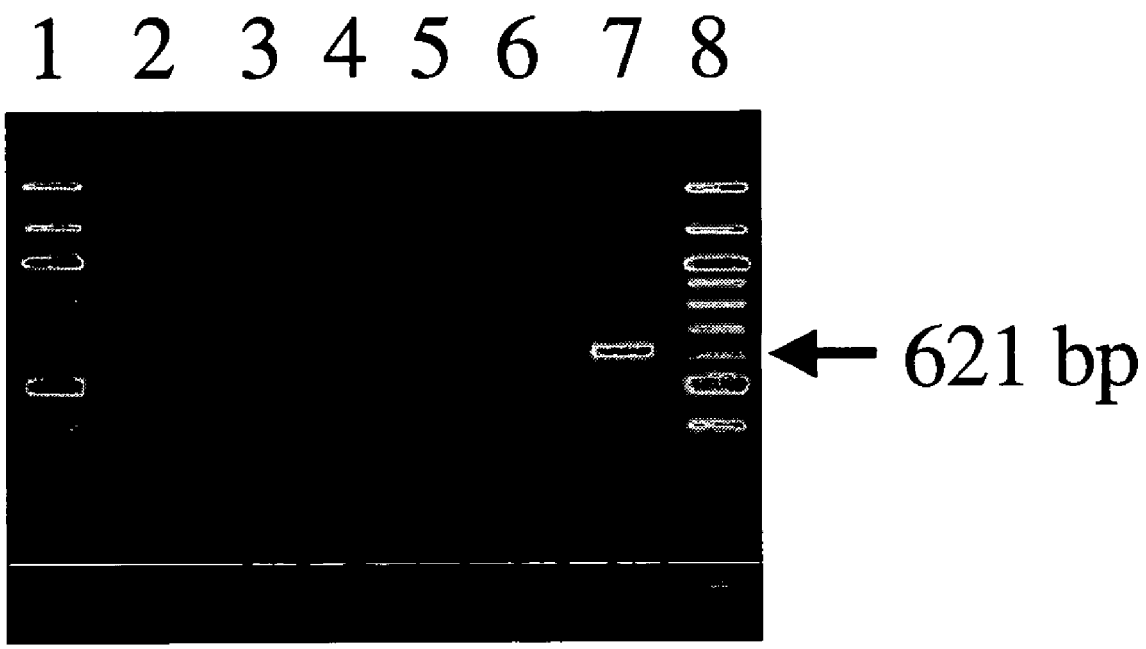
FIG. 9: PCR detection of site-specific gene insertion in the absence of Vpr-Cre. G418-resistant colonies from YY2 cells that had been transduced with a targeting vector containing no Vpr-Cre were pooled and analyzed by PCR. No PCR product was observed in any of the lanes. Lanes are designated as follows: 1) DNA size standards; 2) amplification of DNA from 400 G418-resistant colonies; 3) amplification of DNA from 1,000 G418-resistant colonies; 4) amplification of DNA from 5,000 G418-resistant colonies; 5) amplification of DNA from 40,000 G418-resistant colonies; 6) amplification of DNA from non-transduced YY2 cells; 7) amplification of DNA from 2,500 G418-resistant colonies transduced with targeting vector containing Vpr-Cre; 8) DNA size standards.

These results suggest that the efficiency of site-specific insertion is between 1/250 and 1/2500 when selected in G418-containing medium. As a control, G418-resistant colonies from YY2 cells transduced with the targeting vector containing no Vpr-Cre were pooled and analyzed by PCR. No 621-bp PCR fragment was observed, even when using a pool made up of 40,000 colonies (FIG. 9, lane 5). This clearly demonstrates that Vpr-Cre must be co-packaged into the vector particle in order for site-specific gene insertion to occur. Since the neo gene in the targeting vector contained no promoter, it is likely that the actual infectious vector titers were underestimated. Since the targeting vector contained the hygromycin-resistance gene controlled by the TK promoter, this vector was titered in YY2 cells with hygromycin-containing medium. It was found that the hygromycin-resistant titers were approximately 10 fold higher than G418-resistant titers. Thus, the efficiency for site-specific insertion was adjusted to be in the range of 1/2,500 (0.04%) and 1/25,000 (0.004%). This estimate is consistent with the efficiency of Cre-IoxP-mediated gene insertion in mammalian cells reported previously (Sauer 1990). The difference is that the present invention utilizes an HIV vector for gene targeting rather than DNA transfection. The presently disclosed viral transduction method of gene targeting overcomes the limitations inherent in transfection, such as poor efficiency in most cell types.

Figure 10:
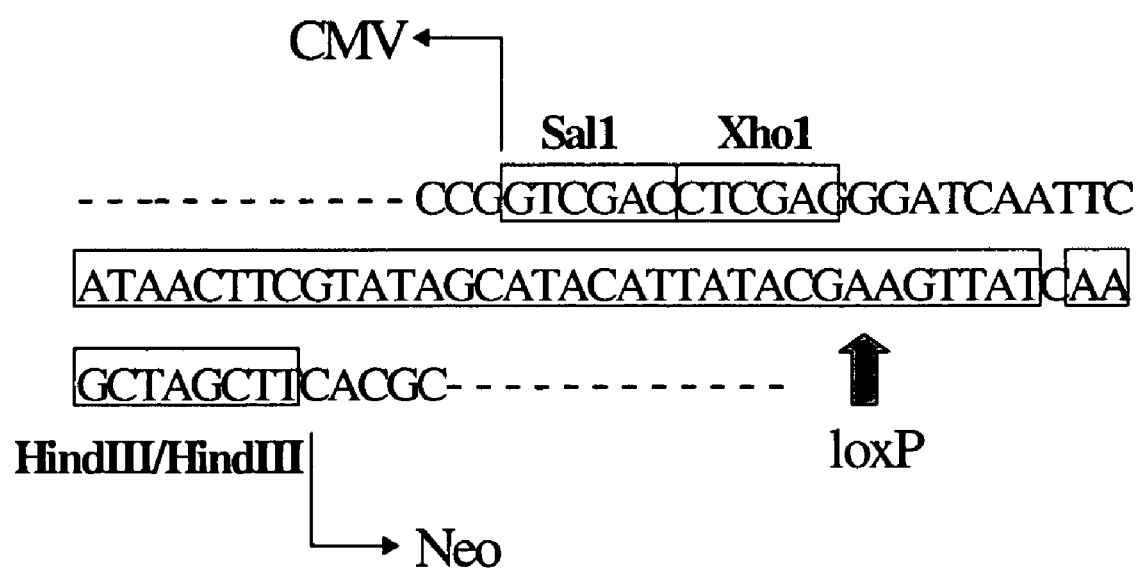
FIG. 10: Sequence analysis of site-specific gene insertional junction. To confirm site-specific gene targeting, the amplified 621-bp fragment from G418-resistant YY2 cells was cloned and sequenced. Shown is the DNA sequence spanning the recombination (loxP) junction (SEQ ID NO:1).

To confirm site-specific gene targeting, the amplified 621-bp fragment was cloned and sequenced. FIG. 10 shows the DNA sequence spanning the recombination (IoxP) junction. This sequence is also set forth in SEQ ID NO: 1. The DNA sequence data confirmed that the neo gene was now positioned immediately downstream from the IoxP site. It is unlikely that the fragment is derived from PCR contamination for two reasons: 1) a plasmid containing the CMV IE promoter followed by the IoxP site and the neo gene did not exist in the lab, and 2) the Sal1 and Xho1 sites shown in FIG. 10 are only originally present in the CMV-IoxP polynucleotide sequence in YY2 cells, while the HindIII/HindIII site is only present in the targeting vector. Since these restriction enzyme sites are now flanking the IoxP site in the PCR fragment, recombination must have taken place to account for this result. The transduction experiment was repeated, and a similar efficiency for site-specific gene insertion was observed (data not shown).

Figure 11:
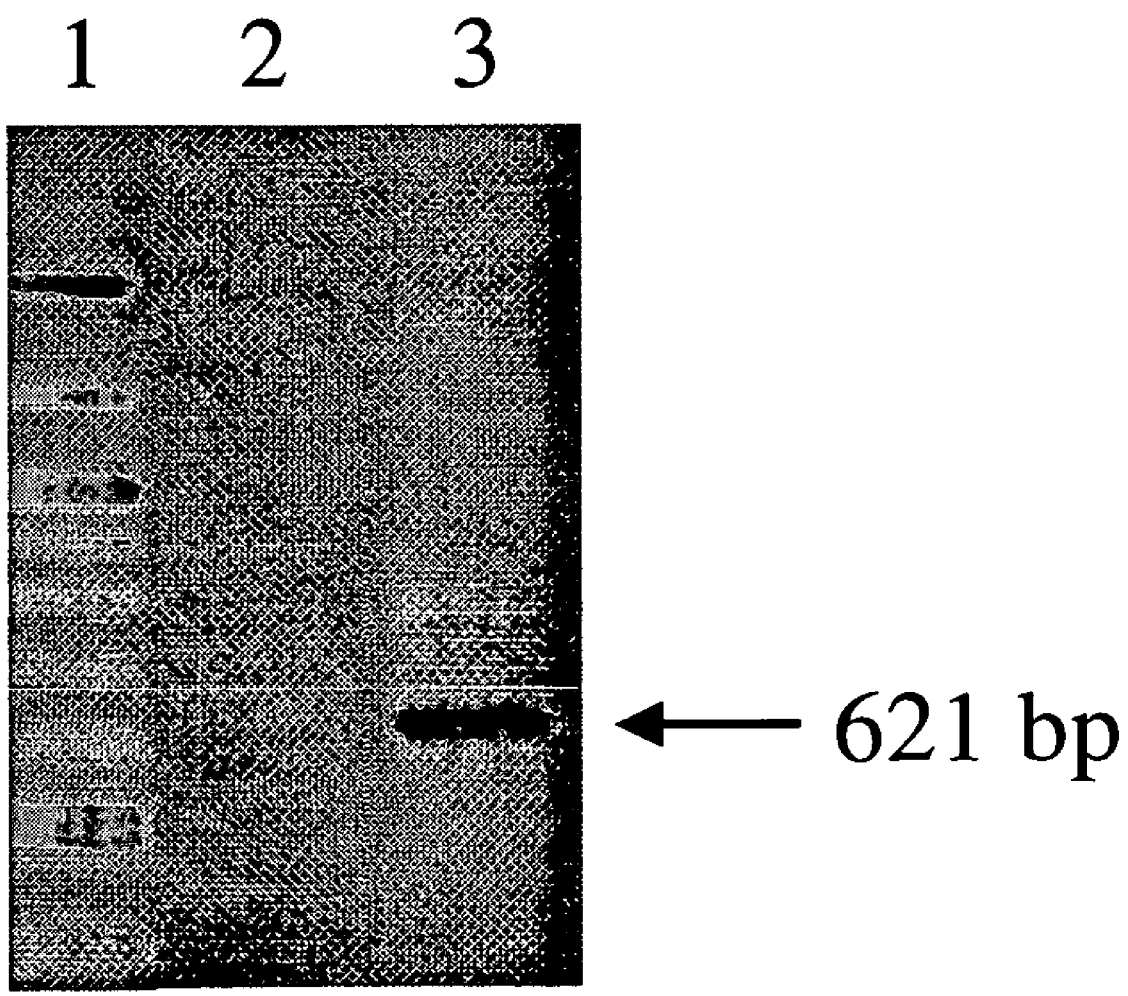
FIG. 11: Enrichment for the site-specific gene insertion with an integrase-deficient targeting vector. To enrich for clones with site-specific gene insertions, a targeting vector deficient in HIV integrase (Int⁻) was generated. Genomic DNA was isolated from a pool of G418-resistant colonies and amplified by PCR to detect insertions. Lanes are designated as follows: 1) DNA size standards; 2) genomic DNA from a pool of three G418-resistant colonies; 3) genomic DNA from a pool of 30 G418-resistant colonies.

To enrich for the clones with site-specific gene insertions, a targeting vector deficient in HIV integrase (Int⁻) was generated (pC-HelpIN, provided by Dr. J. Riser, NIH, Bethesda, Md.) (Mochizuki 1998). Since normal HIV integration was inhibited in this target vector, site-specific insertion of the neo gene through the Cre-IoxP system was the only way to confer G418-resistance to the cell. It was hypothesized that this approach would enrich the YY2 clones containing site-specific neo insertions and might allow direct isolation of such clones. As predicted, when the Int⁻ targeting vector was generated, its neo titer decreased by at least three orders of magnitude compared to the titer of the targeting vector containing the wild-type integrase. Genomic DNA from a pool of three G418-resistant colonies failed to show site-specific insertion, as determined by the absence of the 621-bp PCR fragment, but a pool of 30 colonies was sufficient to show the PCR band (FIG. 11, lanes 2 & 3). The amplified 621-bp fragment was cloned and sequenced. The result was identical to the sequence set forth in FIG. 10, confirming specific insertion of the neo gene into the target IoxP site in the YY2 genome. Since only 30 colonies were required to observe site-specific insertion, this sequence information may allow for direct isolation of individual clones containing a site-specific recombination event.

Example 4

Incorporation of SceI into HIV Particles

Figure 12:
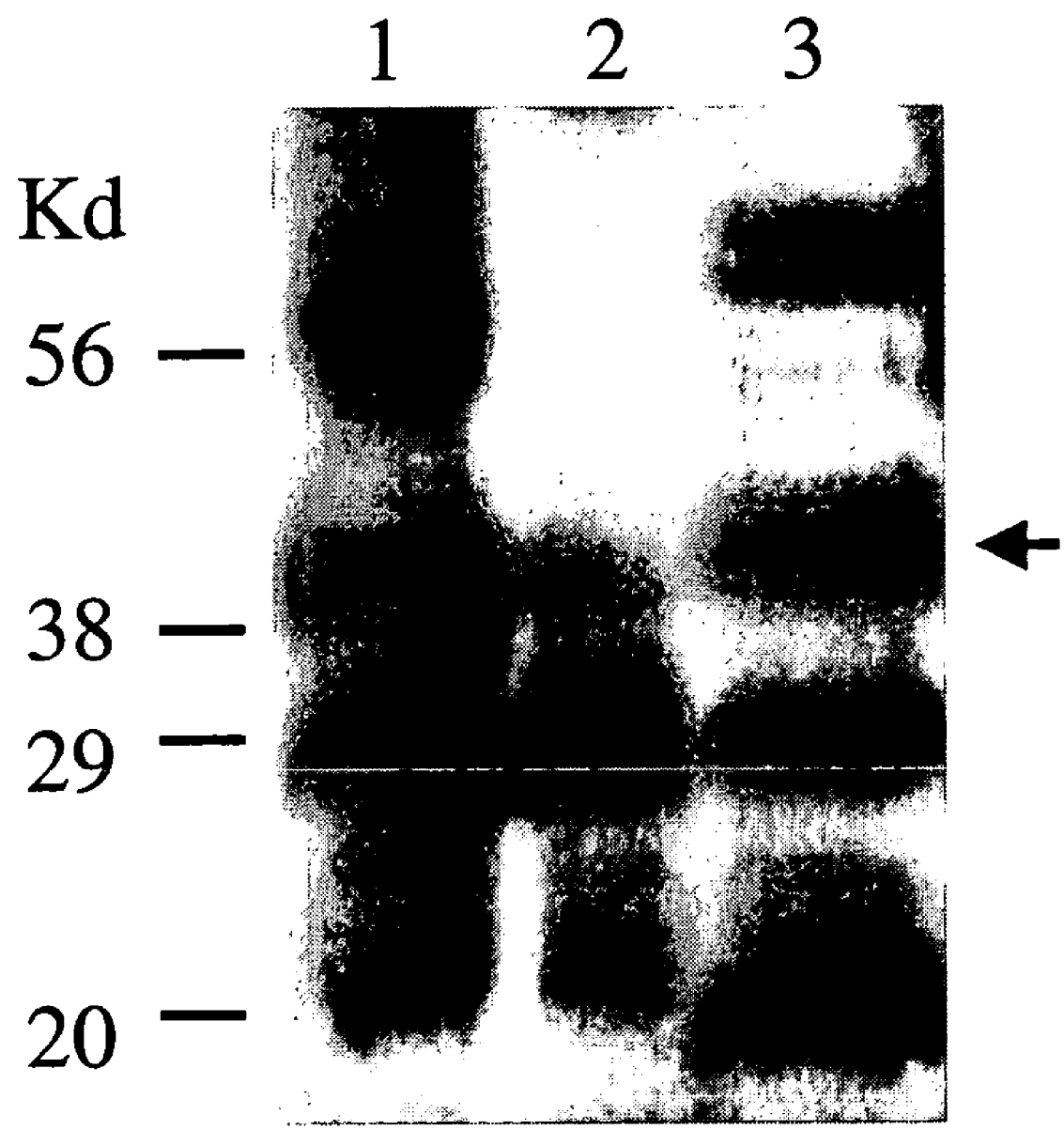
FIG. 12: Incorporation of Vpr-SceI into HIV vector particles. An expression plasmid encoding a Vpr-SceI fusion protein was co-transfected with pCMV-HIVΔvpr into 293T cells. Viral particles were harvested after 40 hours, partially purified by centrifugation through a sucrose cushion, and analyzed by Western blot. Vpr-SceI was detected in the viral particles prepared from this co-transfection and in the cell extract of the co-transfected cells. Lanes are designated as follows: 1) viral particles from cells co-transfected with Vpr-SceI and pCMV-HIVΔvpr; 2) viral particles from cells transfected with pCMV-HIVΔvpr only; 3) cell extract from cells co-transfected with Vpr-SceI and pCMV-HIVΔvpr. The arrow indicates the expected position of Vpr-SceI.

To determine whether SceI, like Cre, can be incorporated into virus particles, a vpr-sceI fusion gene was created. The expression plasmid for this gene was co-transfected along with pCMV-HIVΔvpr into 293T cells. The viral particles were harvested 40 hours later and subjected to Western blot analysis after partial purification by centrifugation through a sucrose cushion. Vpr-SceI was detected in the viral particles prepared from this co-transfection (FIG. 12, lane 1) and in the cell extract of the transfected cells (FIG. 12, lane 3). This raises the possibility that, like the Vpr-Cre protein, the Vpr-SceI protein can be delivered by HIV vector transduction. After delivery, the Vpr-SceI should be able to create a double-strand DNA break on a target SceI site in the host genome and facilitate homologous recombination between the vector sequence and its target.

Example 5

Vpr-SceI-Mediated Homologous Recombination

Figure 13:
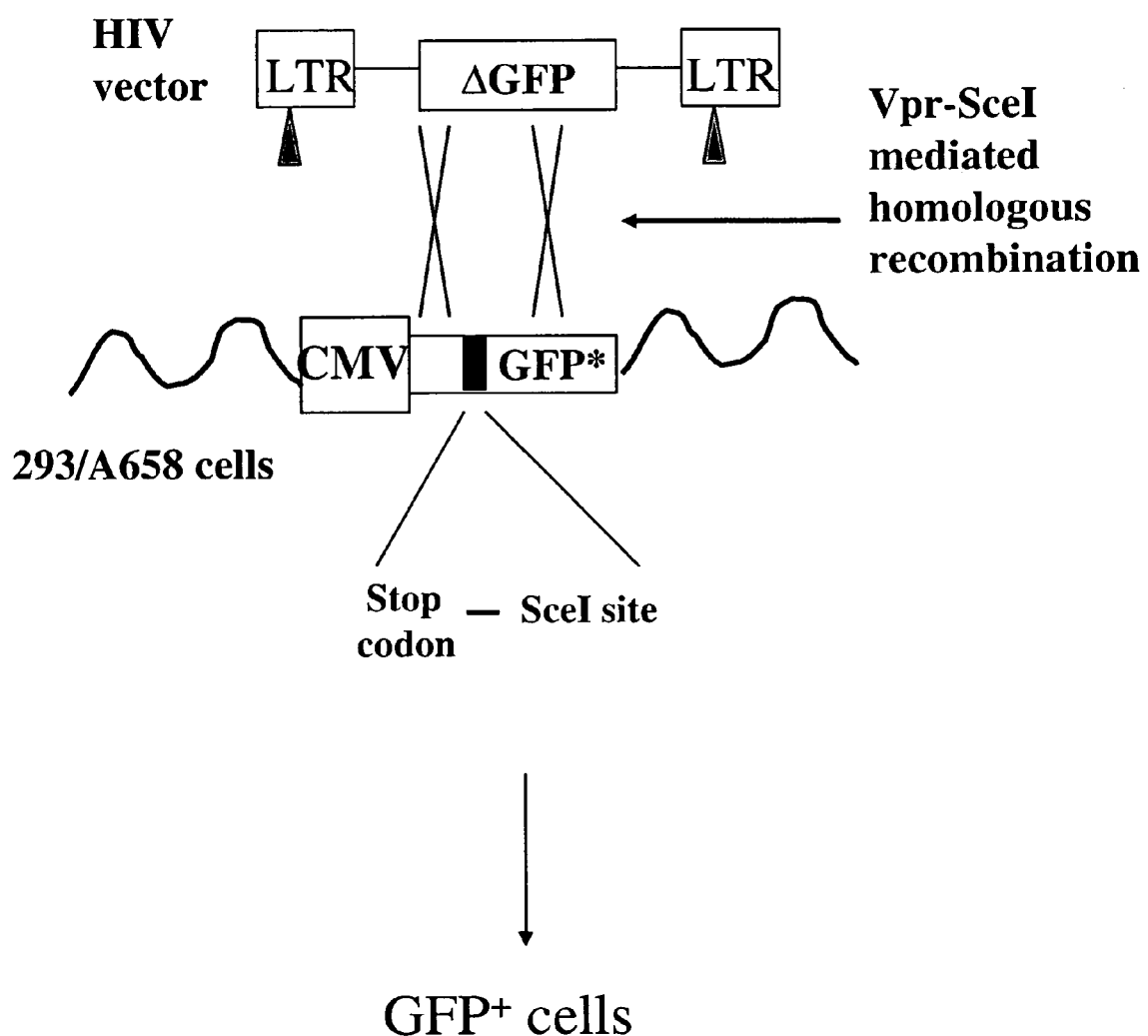
FIG. 13: Vpr-SceI mediated homologous recombination. An HIV vector containing a promoter-less GFP gene (ΔGFP) and the Vpr-SceI fusion protein will be used to transduce 293/A658 cells. 293/A658 cells contain a single copy of an integrated gene target consisting of a mutated GFP gene (GFP★) downstream from the CMV IE promoter. The ΔGFP gene lacks a 37 nucleotide segment that includes the initiation codon for the GFP gene. The GFP★ gene includes an inserted in-frame stop codon and an I-SceI recognition site at base pair 327. 293/A658 cells are GFP⁻ in the absence of recombination. Transduction of the cells with the HIV vector will result in cleavage of the I-SceI site in the host cells due to the presence of Vpr-SceI. The resultant double-stranded DNA break should stimulate homologous recombination between the defective host GFP gene and the defective vector GFP gene, resulting in 293/A658 cells that are GFP⁺.
Figure 14:
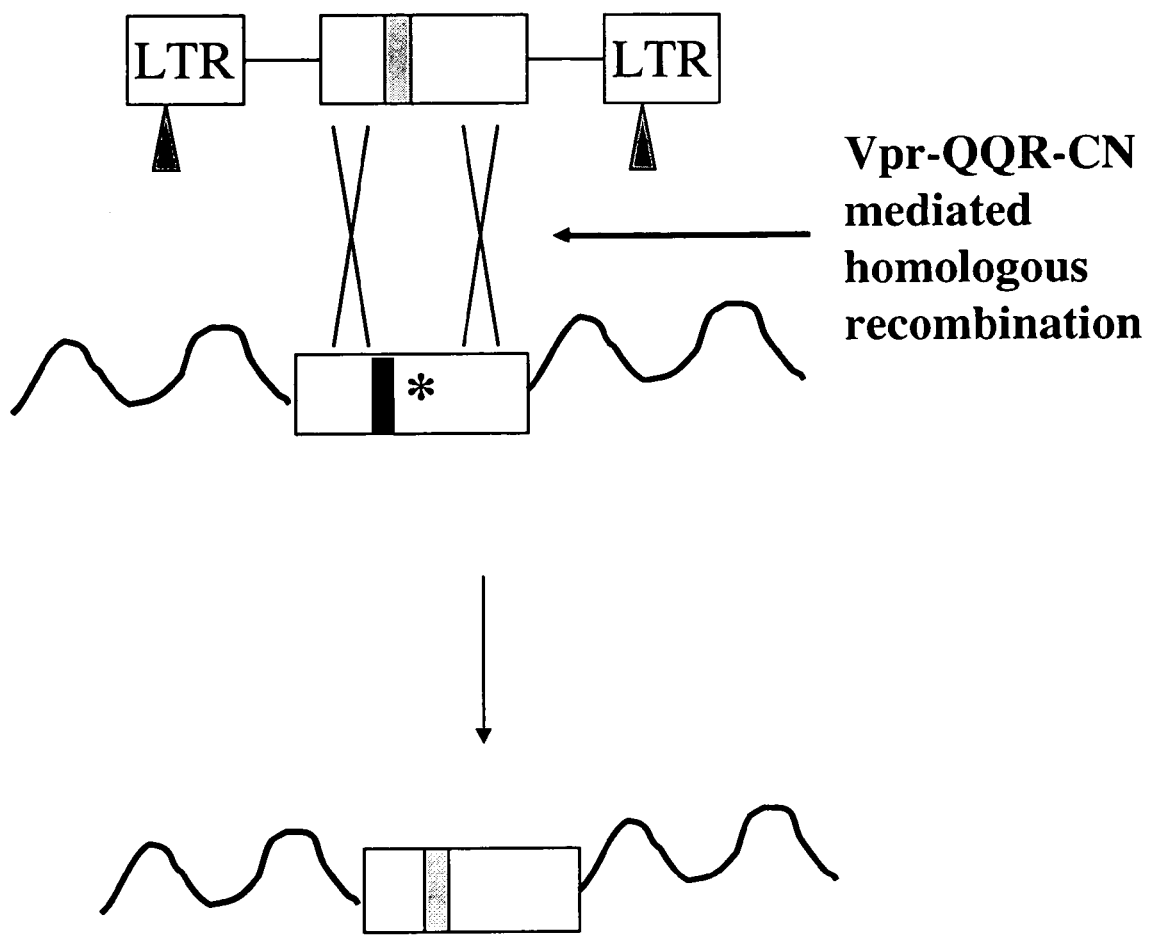
FIG. 14: Vpr-chimeric nuclease mediated homologous recombination. A chimeric nuclease will be utilized to facilitate site-specific gene insertion by homologous recombination in host cells lacking a SceI recognition site. Cells containing a recognition site for a particular endonuclease will be transduced with a lentiviral vector containing a fusion protein. This fusion protein consists of Vpr fused to the chimeric nuclease QQR-CN. QQR-CN consists of a zinc finger DNA binding domain fused to an appropriate site-specific endonuclease. Transduction of a host cell will result in double-stranded cleavage of the host cell DNA at a site specifically recognized by the endonuclease component of Vpr-QQR-CN. This will stimulate homologous recombination between the lentiviral vector and the host genome, resulting in site-specific insertion of an exogenous polynucleotide sequence. Since the lentiviral vector will also contain the endonuclease recognition sequence, it will need to be mutated in such a way that it is no longer recognized by the endonuclease but still encodes the same amino acid sequence.

For Vpr-SceI homologous recombination, the lentiviral vector will contain a promoter-less GFP gene with the first 37 nucleotides removed (FIG. 13). The removed 37 nucleotide segment includes the initiation codon for the GFP gene. The vector will be generated from 293T cells in the presence of Vpr-SceI, and then used to transduce 293/A658 cells. This cell line contains a single copy of an integrated gene target (A658), which consists of a GFP gene mutated by the insertion of an in-frame stop codon and an I-SceI recognition site at base pair 327 of the GFP coding region. The GFP gene is downstream from the CMV IE promoter, but the cell line remains GFP negative in the absence of recombination due to the presence of the stop codon and I-SceI recognition site. Transduction of the cells with a lentiviral vector including Vpr-SceI will result in cleavage of the I-SceI site in the host cells. The resultant double-stranded DNA break should stimulate homologous recombination between the defective host GFP gene and the defective vector GFP gene greater than 2000-fold based on previous results (Porteus 2003). This homologous recombination will result in 293/A658 cells that are positive for GFP.

Example 6

Vpr-Chimeric Nuclease-Mediated Homologous Recombination

The system described in Example 5 depends on the presence of a SceI-recognition site in the host cell. In order to facilitate site-specific gene insertion in cells that do not have SceI recognition sites, chimeric nucleases will be utilized. For example, QQR is an artificial zinc finger DNA binding domain that recognizes the sequence 5'-GGGGAAGAA-3' (SEQ ID NO:2) with nanomolar affinity. QQR can be fused with an endonuclease to generate the chimeric nuclease QQR-CN. A chimeric nuclease consisting of QQR fused to the Fok nuclease has been shown to stimulate homologous recombination and gene targeting more than 2,000-fold in 293 cells. Vpr can be fused to the amino or carboxy terminus of QQR-CN, which will allow the entire fusion protein to be packaged into HIV particles. Transduction of a host cell with a lentiviral vector that includes Vpr-QQR-CN will result in double-stranded cleavage of the host cell DNA at a site specifically recognized by the endonuclease component of Vpr-QQR-CN. This will stimulate homologous recombination between the lentiviral vector and the host genome, resulting in site-specific insertion of an exogenous polynucleotide sequence. Since the lentiviral vector will also contain the endonuclease recognition sequence, it will need to be mutated in such a way that it is no longer recognized by the endonuclease but still encodes the same amino acid sequence.

As stated above, the foregoing are merely intended to illustrate the various embodiments of the present invention. As such, the specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

REFERENCES

1. Abremski, K., Hoess, R., Sternberg, N. 1983. Studies on the properties of P1 site-specific recombination: evidence for topologically unlinked products following recombination. Cell 32:1301-1311.
2. An, D. S., et al. 2000. Marking and gene expression by a lentivirus vector in transplanted human and nonhuman primate CD34(+) cells. J Virol 74:1286-1295.
3. Bibikova, M., et al. 2001. Stimulation of homologous recombination through targeted cleavage by chimeric nucleases. Mol Cell Biol 21:289-297.
4. Bibikova, M., Golic, M., Golic, K. G., Carroll, D. 2002. Targeted chromosomal cleavage and mutagenesis in *Drosophila* using zinc-finger nucleases. Genetics 161: 1169-1175.
5. Bibikova, M., Beumer, K., Trautman, J. K., Carroll, D. 2003. Enhancing gene targeting with designed zinc finger nucleases. Science 300:764.
6. Buchholz, F., Stewart, A. F. 2001. Alteration of Cre recombinase site specificity by substrate-linked protein evolution. Nat Biotech 19:1047-1052.
7. Capecchi, M. R. 1989. Altering the genome by homologous recombination. Science 244:1288-1292.
8. Case, S. S., et al. 1999.Stable transduction of quiescent CD34(+)CD38(−) human hematopoietic cells by HIV-1-based lentiviral vectors. Proc Natl Acad Sci USA 96:2988-2993.
9. Chandrasegaran, S., Smith, J. 1999. Chimeric restriction enzymes: what is next? Biol Chem 380:841-848.
10. Choulika, A., Perrin, A., Dujon, B., Nicolas, J. F. 1995. Induction of homologous recombination in mammalian chromosomes by using the I-SceI system of *Saccharomyces cerevisiae*. Mol Cell Biol 15:1968-1973.
11. Cohen-Tannoudji, M., et al. 1998. I-SceI-induced gene replacement at a natural locus in embryonic stem cells. Mol Cell Biol 18:1444-1448.
12. Elliott, B., et al. 1998. Gene conversion tracts from double-strand break repair in mammalian cells. Mol Cell Biol 18:93-101.
13. Evans, J. T., Kelly, P. F., O'Neill, E., Garcia, J. V. 1999. Human cord blood CD34+CD38-cell transduction via lentivirus-based gene transfer vectors. Hum Gene Ther 10:1479-1489.
14. Gallay, P., Hope, T., Chin, D., Trono, D. 1997. HIV-1 infection of nondividing cells through the recognition of integrase by the importin/karyopherin pathway. Proc Natl Acad Sci USA 94:9825-9830.
15. Haas, D. L., Case, S. S., Crooks, G. M., Kohn, D. B. 2000. Critical factors influencing stable transduction of human CD34(+) cells with HIV-1-derived lentiviral vectors. Mol Ther 2:71-80.

16. Hacein-Bey-Abina, S., et al. 2003. LMO2-associated clonal T cell proliferation in two patients after gene therapy for SCID-X1. Science 302:415-419.

17. Heinzinger, N. K., et al. 1994. The Vpr protein of human immunodeficiency virus type 1 influences nuclear localization of viral nucleic acids in nondividing host cells. Proc Natl Acad Sci USA 91:7311-7315.

18. Hoess, R. H., Wierzbicki, A., Abremski, K. 1986. The role of the loxP spacer region in P1 site-specific recombination. Nucleic Acids Res 14:2287-2300.

19. Horn, P. A., et al. 2002a. Lentivirus-mediated gene transfer into hematopoietic repopulating cells in baboons. Gene Ther 9:1464-1471.

20. Horn, P. A., et al. 2002b. Highly efficient gene transfer into baboon marrow repopulating cells using GALV-pseudotype oncoretroviral vectors produced by human packaging cells. Blood 100:3960-3967.

21. Kafri, T., et al. 1997. Sustained expression of genes delivered directly into liver and muscle by lentiviral vectors. Nat Genet 17:314-317.

22. Koller, B. H., Smithies, O. 1992. Altering genes in animals by gene targeting. Annu Rev Immunol 10:705-730.

23. Li, Z., et al. 2002. Murine leukemia induced by retroviral gene marking. Science 296:497.

24. Miller, D. G., Adam, M. A., Miller, A. D. 1990. Gene transfer by retrovirus vectors occurs only in cells that are actively replicating at the time of infection. Mol Cell Biol 10:4239-4242.

25. Miller, M. D., Farnet, C. M., Bushman, F. D. 1997. Human immunodeficiency virus type 1 preintegration complexes: studies of organization and composition. J Virol 71:5382-5390.

26. Miyoshi, H., Takahashi, M., Gage, F. H., Verma, I. M. 1997. Stable and efficient gene transfer into the retina using an HIV-based lentiviral vector. Proc Natl Acad Sci USA 94:10319-10323.

27. Miyoshi, H., et al. 1999. Transduction of human CD34+ cells that mediate long-term engraftment of NOD/SCID mice by HIV vectors. Science 283:682-686.

28. Mochizuki, H., et al. 1998. High-titer human immunodeficiency virus type 1-based vector systems for gene delivery into nondividing cells. J Virol 72:8873-8883.

29. Naldini, L., et al. 1996. Efficient transfer, integration, and sustained long-term expression of the transgene in adult rat brains injected with a lentiviral vector. Proc Natl Acad Sci USA 93:11382-11388.

30. Poeschla, E. M., Wong-Staal, F., Looney, D. J. 1998. Efficient transduction of nondividing human cells by feline immunodeficiency virus lentiviral vectors. Nat Med 4:354-357.

31. Popov, S., et al. 1998a. Viral protein R regulates docking of the HIV-1 preintegration complex to the nuclear pore complex. J Biol Chem 273:13347-13352.

32. Popov, S., et al. 1998b. Viral protein R regulates nuclear import of the HIV-1 pre-integration complex. EMBO J 17:909-917.

33. Porteus, M. H., Baltimore, D. 2003. Chimeric nucleases stimulate gene targeting in human cells. Science 300:763.

34. Richardson, C., Moynahan, M. E., Jasin, M. 1998. Double-strand break repair by interchromosomal recombination: suppression of chromosomal translocations. Genes Dev 12:3831-3842.

35. Rouet, P., Smih, F., Jasin, M. 1994. Introduction of double-strand breaks into the genome of mouse cells by expression of a rare-cutting endonuclease. Mol Cell Biol 14:8096-8106.

36. Salmon, P., et al. 2000. High-level transgene expression in human hematopoietic progenitors and differentiated blood lineages after transduction with improved lentiviral vectors. Blood 96:3392-3398.

37. Sauer, B., Henderson, N. 1990. Targeted insertion of exogenous DNA into the eukaryotic genome by the Cre recombinase. New Biol 2:441-449.

38. Sauer, B. 1993. Manipulation of transgenes by site-specific recombination: use of Cre recombinase. Methods Enzymol 225:890-900.

39. Schroder, A. R., et al. 2002. HIV-1 integration in the human genome favors active genes and local hotspots. Cell 110:521-529.

40. Smith, J., et al. 2000. Requirements for double-strand cleavage by chimeric restriction enzymes with zinc finger DNA-recognition domains. Nucleic Acids Res 28:3361-3369.

41. Sternberg, N. 1981a. Bacteriophage P1 site-specific recombination. III. Strand exchange during recombination at lox sites. J Mol Biol 150:603-608.

42. Sternberg, N., Hamilton, D. 1981b. Bacteriophage P1 site-specific recombination. I. Recombination between loxP sites. J Mol Biol 150:467-486.

43. Sternberg, N., Hamilton, D., Hoess, R. 1981c. Bacteriophage P1 site-specific recombination. II. Recombination between loxP and the bacterial chromosome. J Mol Biol 150:487-507.

44. Sutton, R. E., et al. 1998. Human immunodeficiency virus type I vectors efficiently transduce human hematopoietic stem cells. J Virol 72:5781-5788.

45. Thomas, K. R., Folger, K. R., Capecchi, M. R. 1986. High frequency targeting of genes to specific sites in the mammalian genome. Cell 44:419-428.

46. Thyagarajan, B., Guimaraes, M. J., Groth, A. C., Calos, M. P. 2000. Mammalian genomes contain active recombinase recognition sites. Gene 244:47-54.

47. Uchida, N., et al. 1998. HIV, but not murine leukemia virus, vectors mediate high efficiency gene transfer into freshly isolated G0/G1 human hematopoietic stem cells. Proc Natl Acad Sci USA 95:11939-11944.

48. Vanin, E. F., et al. 1997. Development of high-titer retroviral producer cell lines by using Cre-mediated recombination. J Virol 71:7820-7826.

49. Woods, N. B., et al. 2003. Lentiviral vector transduction of NOD/SCID repopulating cells results in multiple vector integrations per transduced cell: risk of insertional mutagenesis. Blood 101:1284-1289.

50. Wu, X., Li, Y., Crise, B., Burgess, S. M. 2003. Transcription start regions in the human genome are favored targets for MLV integration. Science 300:1749-1751.

51. Zheng, H., Wilson, J. H. 1990. Gene targeting in normal and amplified cell lines. Nature 344:170-173.

What is claimed is:

1. A lentiviral-based targeting vector for site-specific insertion of an exogenous polynucleotide sequence into a host genome comprising the exogenous polynucleotide sequence, a lentiviral polynucleotide sequence, and a fusion protein capable of stimulating homologous recombination.

2. The targeting vector of claim 1, wherein said fusion protein comprises a DNA binding domain fused to an endonuclease domain.

3. The targeting vector of claim 1, wherein said fusion protein comprises an HIV preintegration complex protein or a portion thereof attached to a protein with site-specific endonuclease activity or a portion thereof.

4. The targeting vector of claim 1 wherein said lentiviral polynucleotide sequence is an HIV polynucleotide sequence.

5. The targeting vector of claim 1, wherein said vector further comprises one or more reporter genes.

6. The targeting vector of claim 2, wherein said fusion protein further comprises an HIV preintegration complex protein or a portion thereof.

7. The targeting vector of claim 2, wherein said DNA binding domain is a zinc finger DNA binding domain.

8. The targeting vector of claim 3, wherein said protein with site-specific endonuclease activity is selected from the group consisting of ScelI, Cre, and a Cre variant.

9. The targeting vector of claim 6 or claim 3, wherein said HIV preintegration complex protein is Vpr.

10. The targeting vector of claim 4, wherein said exogenous polynucleotide sequence is located in the U3 region of the 3' LTR of said HIV polynucleotide sequence.

11. A method for inserting an exogenous polynucleotide sequence into a host genome in a site-specific manner, comprising transducing a host cell with a lentiviral-based targeting vector comprising the exogenous polynucleotide sequence, a lentiviral polynucleotide sequence, and a fusion protein capable of stimulating homologous recombination.

12. The method of claim 11, wherein said fusion protein comprises a DNA binding domain fused to an endonuclease domain.

13. The method of claim 11, wherein said fusion protein comprises an HIV preintegration complex protein or a portion thereof attached to a protein with site-specific endonuclease activity or a portion thereof.

14. The method of claim 11, wherein said lentiviral polynucleotide sequence is an HIV polynucleotide sequence.

15. The method of claim 11, wherein said targeting vector further comprises one or more reporter genes.

16. The method of claim 12, wherein said fusion protein further comprises an HIV preintegration complex protein or a portion thereof.

17. The method of claim 12, wherein said DNA binding domain is a zinc finger DNA binding domain.

18. The targeting vector of claim 13, wherein said protein with site-specific endonuclease activity is selected from the group consisting of Scel, Cre, and a Cre variant.

19. The method of claim 16 or claim 13, wherein said HIV preintegration complex protein is Vpr.

20. The method of claim 14, wherein said exogenous polynucleotide sequence is located in the U3 region of the 3' LTR of said HIV polynucleotide sequence.

21. A fusion protein comprising the HIV preintegration complex protein Vpr attached to the amino or carboxy terminus of the Cre protein or a Cre variant.

22. A fusion protein comprising the HIV preintegration complex protein Vpr attached to Scel.

23. A fusion protein comprising the HIV preintegration complex protein Vpr attached to a chimeric nuclease, wherein said chimeric nuclease comprises a DNA binding domain attached to an endonuclease domain.

* * * * *